(12) United States Patent
Huang

(10) Patent No.: US 11,992,844 B2
(45) Date of Patent: May 28, 2024

(54) DRIED REAGENT STRAINERS AND METHODS FOR MAKING AND USING THE SAME

(71) Applicant: Becton, Dickinson and Company, Franklin Lakes, NJ (US)

(72) Inventor: Wei Huang, Cupertino, CA (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 539 days.

(21) Appl. No.: 16/653,390

(22) Filed: Oct. 15, 2019

(65) Prior Publication Data

US 2020/0147615 A1    May 14, 2020

Related U.S. Application Data

(60) Provisional application No. 62/760,817, filed on Nov. 13, 2018.

(51) Int. Cl.
*B01L 3/00* (2006.01)
*G01N 15/14* (2006.01)
*G01N 33/58* (2006.01)

(52) U.S. Cl.
CPC .............. *B01L 3/523* (2013.01); *G01N 15/14* (2013.01); *G01N 33/583* (2013.01); *B01L 2300/042* (2013.01); *B01L 2300/0681* (2013.01); *B01L 2300/0829* (2013.01)

(58) Field of Classification Search
None
See application file for complete search history.

(56) References Cited

U.S. PATENT DOCUMENTS

| | | |
|---|---|---|
| 3,759,374 A | 9/1973 | Helger et al. |
| 3,891,507 A | 6/1975 | Breuer et al. |
| 3,992,811 A | 11/1976 | Yellin |
| 3,999,948 A | 12/1976 | Diendoerfer et al. |
| 4,142,033 A | 2/1979 | Witenhafer |
| 4,193,980 A | 3/1980 | Clason et al. |
| 4,210,418 A | 7/1980 | Brown |
| 4,222,379 A | 9/1980 | Smith |
| 4,808,539 A | 2/1989 | Chapoteau et al. |
| 4,916,078 A | 4/1990 | Klose et al. |

(Continued)

FOREIGN PATENT DOCUMENTS

| | | |
|---|---|---|
| CN | 102841195 A | 12/2012 |
| CN | 104704363 A | 6/2015 |

(Continued)

OTHER PUBLICATIONS

Becton, Dickinson and Company, "BD Horizon Brilliant Dyes", 2021, Internet, URL: https://www.bdbiosciences.com/en-us/applications/research-applications/multicolor-flow-cytometry/brilliant-violet-dyes.

(Continued)

*Primary Examiner* — Matthew D Krcha
(74) *Attorney, Agent, or Firm* — Nicholas D. Cervenka; Bret E. Field; BOZICEVIC, FIELD & FRANCIS LLP

(57) ABSTRACT

Dried reagent strainers, such as cell strainers are provided. Aspects of the strainers include a body having an opening with a filter positioned in the opening, where the filter includes a dried reagent composition. Aspects of the invention further include methods of making and using the strainers, as well as kits containing the strainers.

19 Claims, 13 Drawing Sheets

(56) References Cited

U.S. PATENT DOCUMENTS

| | | | |
|---|---|---|---|
| 4,919,890 A | 4/1990 | Arai et al. | |
| 5,073,484 A | 12/1991 | Swanson et al. | |
| 5,213,505 A | 5/1993 | Laipply | |
| 5,225,285 A | 7/1993 | Hall | |
| 5,354,654 A | 10/1994 | Ligler et al. | |
| 5,384,411 A | 1/1995 | Robotti et al. | |
| 5,518,612 A | 5/1996 | Kayal et al. | |
| 5,593,587 A * | 1/1997 | Fumihiko | B01D 29/085 210/470 |
| 5,601,728 A | 2/1997 | Kayal et al. | |
| 5,711,875 A | 1/1998 | Kayal et al. | |
| 5,945,341 A | 8/1999 | Howard | |
| 6,221,655 B1 * | 4/2001 | Fung | B01L 3/5021 422/504 |
| 6,350,619 B1 | 2/2002 | Mercolino et al. | |
| 7,141,436 B2 | 11/2006 | Getto-Menking et al. | |
| 7,144,950 B2 | 12/2006 | Bazan et al. | |
| 7,211,443 B2 | 5/2007 | Woudenberg et al. | |
| 7,214,489 B2 | 5/2007 | Bazan et al. | |
| 7,270,956 B2 | 9/2007 | Bazan et al. | |
| 7,332,329 B2 | 2/2008 | Wark et al. | |
| 7,629,448 B2 | 12/2009 | Bazan et al. | |
| 7,666,594 B2 | 2/2010 | Bazan et al. | |
| 7,695,953 B2 | 4/2010 | Gould et al. | |
| 7,807,448 B2 | 10/2010 | Glezer et al. | |
| 7,811,755 B2 | 10/2010 | Bazan et al. | |
| 7,842,475 B2 | 11/2010 | Zheng et al. | |
| 7,867,751 B2 | 1/2011 | Jia et al. | |
| 7,897,684 B2 | 3/2011 | Bazan et al. | |
| 7,914,984 B2 | 3/2011 | Bazan et al. | |
| 7,972,838 B2 | 7/2011 | Korpimaki et al. | |
| 8,101,416 B2 | 1/2012 | Bazan et al. | |
| 8,110,673 B2 | 2/2012 | Bazan et al. | |
| 8,158,444 B2 | 4/2012 | Gaylord et al. | |
| 8,216,530 B2 | 7/2012 | Handique et al. | |
| 8,227,187 B2 | 7/2012 | Bazan et al. | |
| 8,298,834 B2 | 10/2012 | Glezer et al. | |
| 8,338,532 B2 | 12/2012 | Bazan et al. | |
| 8,354,239 B2 | 1/2013 | Gaylord et al. | |
| 8,362,193 B2 | 1/2013 | Gaylord et al. | |
| 8,394,626 B2 | 3/2013 | Ramsey et al. | |
| 8,455,613 B2 | 6/2013 | Gaylord et al. | |
| 8,546,081 B2 | 10/2013 | Bazan et al. | |
| 8,575,303 B2 | 11/2013 | Gaylord et al. | |
| 8,609,044 B2 | 12/2013 | Ullin et al. | |
| 8,617,814 B2 | 12/2013 | Bazan et al. | |
| 8,669,055 B2 | 3/2014 | Bazan et al. | |
| 8,759,444 B2 | 6/2014 | Bazan et al. | |
| 8,771,615 B2 | 7/2014 | Lee-Smith et al. | |
| 8,802,450 B2 | 8/2014 | Gaylord et al. | |
| 8,835,113 B2 | 9/2014 | Bazan et al. | |
| 8,841,072 B2 | 9/2014 | Bazan et al. | |
| 8,857,282 B2 | 10/2014 | Lee-Smith | |
| 8,969,509 B2 | 3/2015 | Liu et al. | |
| 8,980,572 B2 | 3/2015 | Wong et al. | |
| 8,993,335 B2 | 3/2015 | Bazan et al. | |
| 9,040,236 B2 | 5/2015 | Hill et al. | |
| 9,085,799 B2 | 7/2015 | Bazan et al. | |
| 9,096,894 B2 | 8/2015 | Iguchi et al. | |
| 9,139,869 B2 | 9/2015 | Gaylord et al. | |
| 9,159,465 B2 | 10/2015 | Bazan et al. | |
| 9,371,559 B2 | 6/2016 | Bazan et al. | |
| 9,383,353 B2 | 7/2016 | Gaylord et al. | |
| 9,442,106 B2 | 9/2016 | Beck et al. | |
| 9,533,136 B2 | 1/2017 | Midgette et al. | |
| 9,547,008 B2 | 1/2017 | Gaylord et al. | |
| 9,857,365 B2 | 1/2018 | Choi et al. | |
| 9,878,323 B2 | 1/2018 | Glezer et al. | |
| 10,046,257 B2 | 8/2018 | Bosio et al. | |
| 10,161,935 B2 | 12/2018 | Fujiwara et al. | |
| 2001/0036423 A1 | 11/2001 | Kawasaki et al. | |
| 2002/0001539 A1 | 1/2002 | Dicesare et al. | |
| 2002/0015663 A1 | 2/2002 | Goldstein | |
| 2003/0006141 A1 * | 1/2003 | Gerlach | B01L 3/5027 204/601 |
| 2003/0012714 A1 | 1/2003 | Taylor et al. | |
| 2003/0108973 A1 | 6/2003 | Gatto-Menking et al. | |
| 2003/0143755 A1 | 7/2003 | Davis et al. | |
| 2003/0207465 A1 | 11/2003 | Davis et al. | |
| 2003/0219908 A1 | 11/2003 | Davis et al. | |
| 2004/0005246 A1 | 1/2004 | Efthimiadis et al. | |
| 2004/0092036 A1 | 5/2004 | Chen et al. | |
| 2006/0040408 A1 | 2/2006 | Jones et al. | |
| 2006/0166367 A1 | 7/2006 | Satoh et al. | |
| 2006/0182655 A1 | 8/2006 | Zou et al. | |
| 2007/0054341 A1 | 3/2007 | Gatto-Menking et al. | |
| 2007/0202538 A1 | 8/2007 | Glezer et al. | |
| 2007/0243601 A1 * | 10/2007 | Korpimaki | C12Q 1/686 435/287.9 |
| 2007/0251337 A1 | 11/2007 | Reed et al. | |
| 2008/0194508 A1 | 8/2008 | Christensen et al. | |
| 2008/0241962 A1 | 10/2008 | Wang | |
| 2008/0274512 A1 * | 11/2008 | Squirrell | G01N 35/10 435/91.2 |
| 2009/0011518 A1 | 1/2009 | Lindberg | |
| 2009/0176213 A1 | 7/2009 | Zheng et al. | |
| 2010/0015628 A1 | 1/2010 | Farchaus et al. | |
| 2010/0172801 A1 | 7/2010 | Pugia et al. | |
| 2010/0184059 A1 | 7/2010 | Lee et al. | |
| 2010/0215548 A1 | 8/2010 | De Luca et al. | |
| 2010/0285520 A1 | 11/2010 | Halverson et al. | |
| 2010/0330684 A1 | 12/2010 | O'Connor | |
| 2011/0015091 A1 | 1/2011 | Glezer et al. | |
| 2011/0257374 A1 | 10/2011 | Gaylord et al. | |
| 2011/0291076 A1 | 12/2011 | Shukla et al. | |
| 2012/0070385 A1 | 3/2012 | Liu | |
| 2012/0183961 A1 | 7/2012 | Han et al. | |
| 2012/0183967 A1 * | 7/2012 | Dressman | C12Q 1/6858 435/6.12 |
| 2012/0252986 A1 | 10/2012 | Liu | |
| 2012/0301943 A1 | 11/2012 | Iguchi et al. | |
| 2013/0052650 A1 * | 2/2013 | Kavanagh | C12Q 1/686 435/6.12 |
| 2013/0065788 A1 | 3/2013 | Glezer et al. | |
| 2013/0089853 A1 | 4/2013 | Li et al. | |
| 2014/0271481 A1 | 9/2014 | Boday et al. | |
| 2014/0302516 A1 | 10/2014 | Chiu et al. | |
| 2014/0319379 A1 | 10/2014 | Manian | |
| 2015/0125882 A1 | 5/2015 | Bornheimer et al. | |
| 2015/0174547 A1 | 6/2015 | Emans et al. | |
| 2015/0226746 A1 | 8/2015 | Bazan et al. | |
| 2016/0266132 A1 | 9/2016 | Gaylord et al. | |
| 2016/0299164 A1 | 10/2016 | Ackerman et al. | |
| 2016/0320415 A1 | 11/2016 | Manneh | |
| 2016/0341720 A1 | 11/2016 | Bazan et al. | |
| 2016/0349267 A1 | 12/2016 | Gaylord et al. | |
| 2017/0010199 A1 | 1/2017 | Halverson et al. | |
| 2017/0023563 A1 | 1/2017 | Hirano et al. | |
| 2017/0115298 A1 | 4/2017 | Gaylord et al. | |
| 2017/0189902 A1 | 7/2017 | Moran | |
| 2017/0307600 A1 | 10/2017 | Sharkey et al. | |
| 2018/0031554 A1 | 2/2018 | Beck et al. | |
| 2018/0078241 A1 | 3/2018 | Moga et al. | |
| 2018/0143108 A1 | 5/2018 | Madsen et al. | |
| 2018/0154353 A1 | 6/2018 | Glezer et al. | |
| 2018/0224460 A1 | 8/2018 | Inokuma et al. | |
| 2018/0344568 A1 | 12/2018 | Williams et al. | |
| 2019/0004075 A1 | 1/2019 | Ackerman et al. | |
| 2019/0083975 A1 | 3/2019 | Diasses et al. | |
| 2020/0147615 A1 | 5/2020 | Huang | |

FOREIGN PATENT DOCUMENTS

| | | |
|---|---|---|
| CN | 105358977 A | 2/2016 |
| EP | 0225703 | 6/1987 |
| EP | 0225703 A2 | 6/1987 |
| EP | 0464942 | 1/1992 |
| EP | 0464942 A1 | 1/1992 |
| JP | H0374405 A | 3/1991 |
| JP | 2013007751 | 1/2013 |
| JP | 2013517374 A | 5/2013 |
| JP | 2013165709 A | 8/2013 |
| JP | 2014001949 | 1/2014 |

(56) References Cited

FOREIGN PATENT DOCUMENTS

| JP | 2015102337 A | | 6/2015 | | |
|---|---|---|---|---|---|
| JP | 2015528114 A | | 9/2015 | | |
| JP | 2020092705 | | 6/2020 | | |
| KR | 101495631 | | 2/2015 | | |
| WO | WO 2004/001379 | A2 | 12/2003 | | |
| WO | WO 2004/077014 | A2 | 9/2004 | | |
| WO | WO 2004/092324 | A2 | 10/2004 | | |
| WO | WO 2005/086617 | A2 | 9/2005 | | |
| WO | WO2005118863 | A2 | 12/2005 | | |
| WO | WO 2006/003423 | A2 | 1/2006 | | |
| WO | WO2006003423 | | 1/2006 | | |
| WO | WO 2006/074471 | A2 | 7/2006 | | |
| WO | WO 2006/074482 | A2 | 7/2006 | | |
| WO | WO 2006/083932 | A2 | 8/2006 | | |
| WO | WO 2008/100344 | A2 | 8/2008 | | |
| WO | WO 2010/151807 | A1 | 12/2010 | | |
| WO | WO 2011/091086 | A1 | 7/2011 | | |
| WO | WO2012027447 | | 3/2012 | | |
| WO | WO2011105507 | | 6/2013 | | |
| WO | WO2015069546 | | 5/2015 | | |
| WO | WO2015175861 A | | 11/2015 | | |
| WO | WO2017123622 | | 7/2017 | | |
| WO | WO-2017123622 | A1 * | 7/2017 | ............ | C12M 23/48 |
| WO | WO2017184629 | | 10/2017 | | |
| WO | WO2017/222998 | | 12/2017 | | |
| WO | WO/2017/222998 | A1 | 12/2017 | | |
| WO | WO2018148098 | | 8/2018 | | |
| WO | WO2020101831 | | 5/2020 | | |

OTHER PUBLICATIONS

Bergeron, et al., "Evaluation of a Dry Format Reagent Alternative for CD4 T-Cell Enumeration for the FACSCount System: A Report on a Moroccan-Canadian Study", Cytometry, 2010, vol. 78B, p. 188-193.

"ReaPan 34845", Jan. 30, 2013 (Jan. 30, 2013). pp. 1-2. Retrieved from the Internet: URL:http://www.demo.reametrix.comjdownload /QMS/Product Inserts/ReaPan34845.pdf.

Hedley et al. "Novel Lymphocyte Screening Tube Using Dried Monoclonal Antibody Reagents," Cytometry Part B: Clinical Cytometry, 2015, vol. 88, No. 6, pp. 361-370.

Thakar et al. "CD4 estimating reagents in dry format are compatible with conventional flow cytometer; FACSCalibur for estimation of absolute CD4 count & percentages," The Indian Journal of Medical Research, vol. 137, No. 2, Feb. 2013, pp. 346-355.

Communication The extended European search report for European Patent Application No. 17786484.0, dated Oct. 24, 2019, 6 pages.

BD Biosciences, "BD Falcon Tubes and Pipets", 2011, 9 pages.

Wang, "Clinical Flow Cytometry", Jianzhong Wang, p. 244 245, Shanghai Science and Technology Press, Aug. 2005.

* cited by examiner

Each cap with different dried reagent spot(s) allowing flexible reagent combinations to be eluted to the bottom of the tube with a single solution addition and centrifugation May contains a base reagent panel on the bottom of the tube

CD4-BV421

CD4-BV510

CD19-BV605

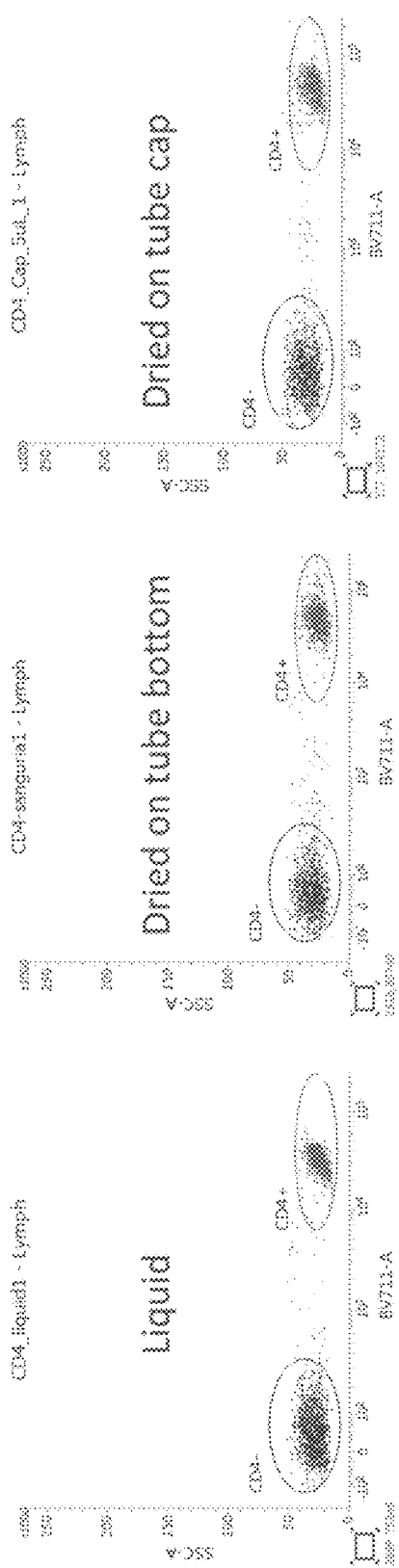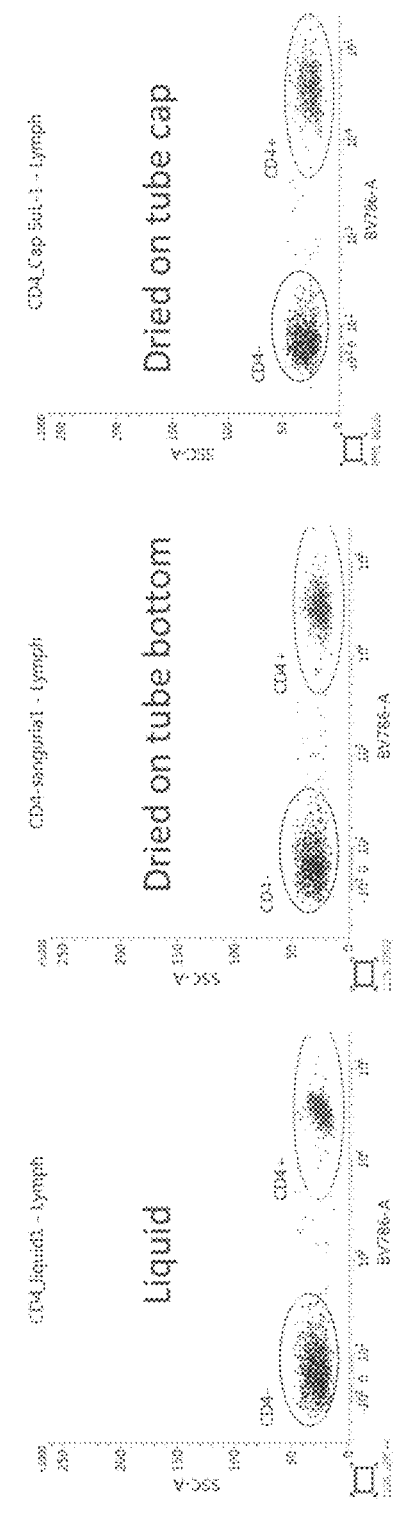

DRIED REAGENT STRAINERS AND METHODS FOR MAKING AND USING THE SAME

CROSS-REFERENCE TO RELATED APPLICATION

Pursuant to 35 U.S.C. § 119(e), this application claims priority to the filing date of U.S. Provisional Patent Application Ser. No. 62/760,817 filed Nov. 13, 2018; the disclosure of which application is herein incorporated by reference.

INTRODUCTION

Assays for determining the presence and concentration of analytes in a liquid biological sample often rely on the specific binding of a detectable label (e.g., comprising a dye moiety conjugated to a specific binding member, such as an antibody) to the target analyte. The detectable label may be a marker that can be visualized either by an unaided eye or detectable by spectroscopy, such as fluorescence or UV-vis spectroscopy. Typically, fluorescent dyes may be used as the detectable label, where the fluorescent dye includes a particular fluorochrome. A fluorochrome may have a certain properties, such as its absorption spectrum, its extinction coefficient at a wavelength convenient for excitation, its emission spectrum, and its quantum efficiency. Quantum efficiency is the number of photons emitted for every photon absorbed.

The properties of a fluorochrome may depend on its surrounding environment. For example, some fluorochromes, such as fluorescein, are sensitive to pH. Fluorescence can also be quenched by an interaction with another molecule in which the emission energy of the dye is dissipated by a non-radiative transition. In some cases, the detectable fluorescence of a fluorochrome can be quenched by interactions between the molecules of another fluorochrome, such as a fluorochrome of another dye. This effect can be observed as an undesirable dye-dye interaction where the fluorescence of a dye is significantly less than would be expected as compared to the dye's fluorescence in the absence of other interfering dyes.

SUMMARY

Dried reagent strainers, such as cell strainers, are provided. Aspects of the strainers include a body having an opening with a filter positioned in the opening, where the filter includes a dried reagent composition. Aspects of the invention further include methods of making and using the strainers, as well as kits containing the strainers.

BRIEF DESCRIPTION OF THE FIGURES

FIGS. 10A to 10E provide provides data obtained from Flow-CAP tubes with dried reagent spots according to an embodiment of the invention, as described in greater detail in the Experimental section, below.

DETAILED DESCRIPTION

Figure 1:
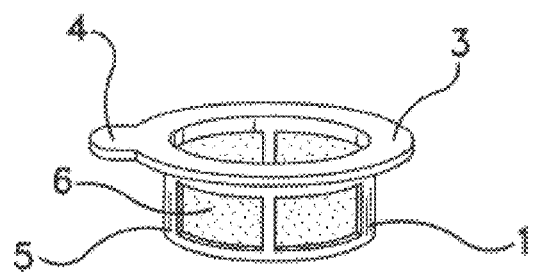
FIG. 1 is a perspective view of a cell strainer and tube according to an embodiment of the invention.
Figure 1:
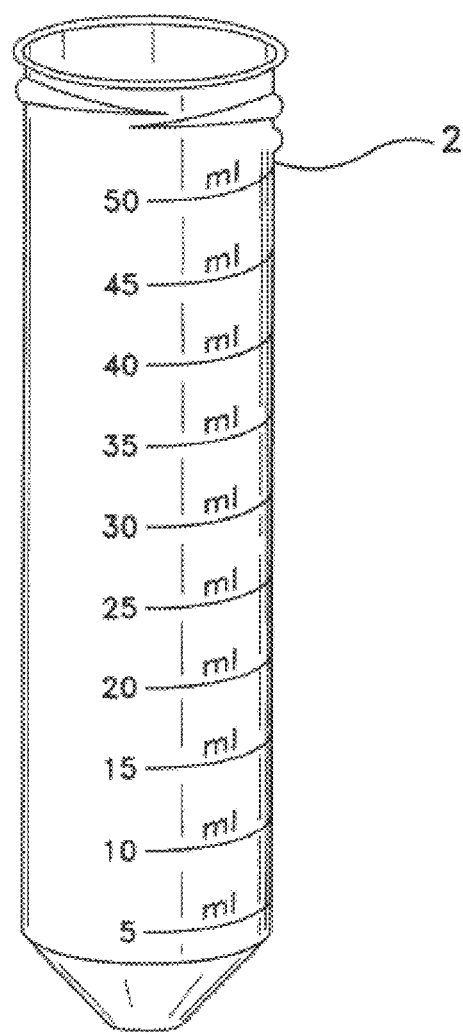

Dried reagent strainers, such as cell strainers are provided. Aspects of the strainers include a body having an opening with a filter positioned in the opening, where the filter includes a dried reagent composition. Aspects of the invention further include methods of making and using the strainers, as well as kits containing the strainers.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

As summarized above, the present disclosure provides dried reagent strainers that include a filter comprising a dried reagent composition. In further describing various embodiments of the invention, the strainers are first reviewed in greater detail. Next, methods of using the strainers are described. In addition, methods of making the strainers, as well as kits that include the strainers, are described further.

DRIED REAGENT STRAINERS

Aspects of the present disclosure include dried reagent strainers. In certain embodiments, the strainers as described herein are useful in assays, for example assays of a liquid sample, such as a biological sample, e.g., for the presence of one or more analytes in the sample.

The term "strainer" as used herein refers to a device that is configured to remove undesired components from a liquid composition by blocking those components from passing through the strainer. Embodiments of the strainers described herein include a body having an opening, e.g., which provides for passage of a liquid through the body, and a filter positioned in the opening, such that liquid passing through the opening also passes through the filter. As the strainers of the invention are dried reagent strainers, the strainers include one or more dried reagent compositions associated with the filters, such that the filters include one or more dried reagent compositions.

The filter component of the strainers may vary. In general, the filter is a structure configured to selectively allow passage of certain components of a liquid but prevent passage of other components of a liquid. In some instances, the filter is configured to allow passage of dissolved substances and single cells of a liquid, but impede, and in some instances prevent, passage of other components of a liquid, such as cellular aggregates, tissues, etc. In some instances, the filter is configured to allow passage of single cells having a volume of 2000 fl or less, such as 1500 fl or less, including 1200 fl or less. In some instances, the filter is configured to impede, and in some instances prevent, passage of a structures having a volume of 2500 fl or greater, such as 5000 fl or greater.

The filter component of the strainer may have any convenient structure, where the filter may be structured as a porous device configured to remove the unwanted components of a liquid passed through it. The pores, i.e., openings or holes, of the filter may vary in size, ranging in some instances from 10 to 200 µm, such as 20 to 150 µm, including 30 to 100 µm, including 20, 35, 40, 70 and 100 µm. Filter structures that may be employed may vary, where in some instances the filter is a planar structure, e.g., a membrane, having the desired porosity, such as described above. In other instances, the filter may be configured as a mesh (i.e., a material made of a network of wire or thread), having the desired porosity, such as described above. The filter may be produced from a variety of different materials, including plastics such as polyamide (PA), polystyrene (PS), polyvinylchloride (PVC), polycarbonate, glass, polyethylene terephthalate (PET), polytetrafluorethylene (PTFE), silicone, poly ethylene (PE), poly propylene (PP) and/or polyvinyl alcohol (PVA), and polyethersulfon (PES).

As reviewed above, dried reagent strainers according to embodiments of the invention include a filter, e.g., as described above, that includes one or more dried reagent compositions. The dried reagent composition may be associated with the filter in any desired way, wherein in some instances the dried reagent composition is associated with the filter such that liquid passing through the filter dissolves the dried reagents so as a produce a reconstituted reagent composition. The dried reagent composition may be positioned at any convenient location of the filter. The dried reagent composition may be positioned on both sides of a filter, or on only one side of a filter, e.g., on the side facing toward the interior surface of a liquid container when the strainer is mated with the container, or on the side facing away from the interior surface of a liquid container when the strainer is mated with the container. A given dried reagent composition is stably associated with the position of the strainer where it is positioned. By stably associated is meant that during handling it does not move but is instead adhered to the position so that it remains at the position during handling. As such, the dried reagent composition is distinguished from a particle of a particle composition that merely touches a location but is not stably positioned, e.g., adhered to, the location.

As summarized above, the filters of the dried reagent strainers of the invention include one or more dried reagent compositions. As such, the filters include at least a first dried reagent composition that includes a reagent stably associated with a location of the filter. The total number of dried reagent compositions may vary as desired. A given filter may include a single dried reagent composition, or a given filter may include 2 or more dried reagent compositions, such as 3 or more, 4 or more, 5 or more, 6 or more, 7 or more, 8 or more, 9 or more, 10 or more, 11 or more, 12 or more, 13 or more, 14 more, 15 or more, 16 or more, 17 or more, 18 or more, 19 or more, 20 or more, 25 or more, 30 or more, 35 or more, 40 or more, 45 or more, 50 or more reagent compositions.

In some embodiments, the filter includes 2 to 200 dried reagent compositions, such as 2 to 100 dried reagent compositions, including 2 to 50 dried reagent compositions, such as 2 to 40, or 2 to 30 or 2 to 20 or 2 to 15, or 2 to 10, or 2 to 7, or 2 to 5 dried reagent compositions. For example, the device may include 2, or 3, or 4, or 5, or 6, or 7, or 8, or 9, or 10, or 11, or 12, or 13, or 14, or 15, or 16, or 17, or 18, or 19, or 20 dried reagent compositions.

A given dried reagent composition may occupy a certain defined area of a filter. While the size of the defined area may vary, ranging from occupying the whole surface area of the filter to only a portion thereof, in some instances the defined area occupied by a given dried reagent composition has a diameter (or longest dimension) ranging from 100 to 10,000μ. Where the filter includes two or more dried reagent compositions, the dried reagent compositions may be distinctly positioned on the filter, such that the two compositions do not overlap, and in some instances are separated by an unoccupied space on the filter, e.g., where the edge of one dried reagent composition is 100 to 10,000μ, such as 1,000 to 5,000μ, from the edge of the another dried reagent composition on the filter.

The dried reagent compositions may include any desired reagent or reagents, such that a given dried reagent composition may include a single reagent or two or more distinct reagents. Reagents of interest include, but are not limited to, dyes, nucleic acids, nucleotides, proteins, peptides, polysaccharides, etc. In some instances, the dried reagent compositions are dye compositions, e.g., as described in greater detail below.

A dried reagent composition is a reagent composition that includes a low amount of solvent. For example, dried reagent compositions may include a low amount of a liquid, such as water. In some cases, a dried reagent composition includes substantially no solvent. For instance, dried reagent compositions may include substantially no liquid, such as water. In certain embodiments, a dried reagent composition includes 25 wt % or less solvent, such as 20 wt % or less, or 15 wt % or less, or 10 wt % or less, or 5 wt % or less, or 3 wt % or less, or 1 wt % or less, or 0.5 wt % or less solvent. In some cases, a dried reagent composition is not a fluid. In some cases, a dried reagent composition is substantially a solid. For example, a dried reagent composition may have a high viscosity, such as a viscosity of 10,000 cP or more, or 25,000 cP or more, or 50,000 cP or more, or 75,000 cP or more, or 100,000 cP or more, or 150,000 cP or more, or 200,000 cP or more, or 250,000 cP or more at standard conditions.

The dried reagent compositions may include one or more non-reagent materials. When present, the non-reagent material is a material compatible with other assay components (e.g., reagents, buffers, analytes, etc.) that may be present in the reagent device during use. The non-reagent material may be substantially inert with respect to the other assay components (e.g., reagents, buffers, analytes, etc.) that may be present in the reagent device during use such that there is no significant reaction between the non-dye material and the other assay components. Examples of non-reagent materials include, but are not limited to, stabilizers, buffers, soluble inert materials (e.g., aqueous soluble inert materials), and the like. Stabilizers of interest include but are not limited to: sugars and polyalcohols. Sugars and polyalcohols suitable for use in lyophilized dye compositions include sugars that are compatible with the other reagents, buffers, dyes and sample components being used. Examples of suitable sugars include, but are not limited to, sucrose, maltose, trehalose, 2-hydroxypropyl-beta-cyclodextrin (β-HPCD), lactose, glucose, fructose, galactose, glucosamine, and the like, and combinations thereof. In certain instances, the sugar is a disaccharide. For example, the disaccharide may be sucrose. Examples of suitable polyalcohols include, but are not limited to, mannitol, glycerol, erythritol, threitol, xylitol, sorbitol, and the like, and combinations thereof. Non-dye materials may include, for example, bovine serum albumin (BSA), sodium azide, glycerol, phenylmethanesulfonyl fluoride (PMSF), ethylenediaminetetraacetic acid (EDTA), buffered citrate, phosphate buffered saline (PBS), sodium chloride, paraformaldehyde, and the like, and combinations thereof.

In some instances, the dried reagent compositions are lyophilized reagent compositions. In certain cases, a lyophilized reagent composition is a reagent composition where water has been removed from the reagent composition by sublimation, where the water in the reagent composition undergoes a phase transition from a solid to a gas. For example, a lyophilized reagent composition may be a reagent composition where water has been removed from the composition by freezing the reagent composition (e.g., freezing water in the reagent composition) and then reducing the pressure surrounding the reagent composition such that the water in the reagent composition undergoes sublimation. In certain instances, a lyophilized reagent composition includes water in a low amount, such as 25% or less, or 20% or less, or 15% or less, or 10% or less, or 9% or less, or 8% or less, or 7% or less, or 6% or less, or 5% or less, or 4% or less, or 3% or less, or 2% or less, or 1% or less, or 0.5% or less, or 0.25% or less, or 0.1% or less water as measured by Karl Fischer (KF) titration. In some cases, a lyophilized reagent composition has 3% or less water as measured by Karl Fischer titration. In some cases, a lyophilized reagent composition has 1% or less water as measured by Karl Fischer titration. In some cases, a lyophilized reagent composition has 0.5% or less water as measured by Karl Fischer titration. Lyophilized reagent compositions may include additives and/or excipients, such as a stabilizer. In some cases, the lyophilized reagent composition includes a stabilizer, such as a sugar or a polyalcohol. Sugars and polyalcohols suitable for use in lyophilized reagent compositions include sugars that are compatible with the other reagents, buffers, dyes and sample components being used. Examples of suitable sugars include, but are not limited to, sucrose, maltose, trehalose, 2-hydroxypropyl-beta-cyclodextrin (β-HPCD), lactose, glucose, fructose, galactose, glucosamine, and the like, and combinations thereof. In certain instances, the sugar is a disaccharide. For example, the disaccharide may be sucrose. Examples of suitable polyalcohols include, but are not limited to, mannitol, glycerol, erythritol, threitol, xylitol, sorbitol, and the like, and combinations thereof.

As summarized above, the reagent in the dried reagent composition is stably associated with the filter of the strainer device. By stably associated is meant that the reagent composition does not readily dissociate from the filter prior to contact with a liquid medium, e.g., an aqueous medium. As such, when associated with the filter in a dried state (e.g., prior to use in an assay), the dried reagent composition remains associated with filter.

In some instances, the filter includes one or more dried dye compositions. Where a given filter includes two or more dried dye compositions, the dried dye compositions may be identical or at least two of the dried dye compositions associated with the filter may be distinct from each other. In certain cases, the filter includes 2 distinct dried dye compositions. In certain cases, the filter includes 5 distinct dried dye compositions. In certain cases, the filter includes 7 distinct dried dye compositions. In certain cases, the filter includes 10 distinct dried dye compositions. Any two dried dye compositions are considered to be distinct if their dye components differ from each other by one or more of molecular formula, excitation maximum and emission maximum. As such, different or distinct dye compositions may differ from each other in terms of chemical composition and/or in terms of one or more properties of the dyes. For instance, different dye compositions may differ from each other by at least one of excitation maxima and emission maxima. In some cases, different dye compositions differ from each other by their excitation maxima. In some cases, different dye compositions differ from each other by their emission maxima. In some cases, different dye compositions differ from each other by both their excitation maxima and emission maxima. As such, in embodiments that include first and second dyes, the first and second dyes may differ from each other by at least one of excitation maxima and emission maxima. For example, the first and second dyes may differ from each other by excitation maxima, by emission maxima, or by both excitation and emission maxima. Additional dye compositions may be included on the filter, where each of the dye compositions on the filter differ from each other as described above. A given pair of dyes may be considered distinct if they differ from each other in terms of excitation or emission maximum, where the magnitude of such difference is, in some instances, 5 nm or more, such 10 nm or more, including 15 nm or more, wherein in some instances the magnitude of the difference ranges from 5 to 400 nm, such as 10 to 200 nm, including 15 to 100 nm, such as 25 to 50 nm.

The dye in the dye composition may be used as a detectable label. In certain cases, the dye includes detectable moieties or markers that are detectible based on, for example, fluorescence emission maxima, fluorescence polarization, fluorescence lifetime, light scatter, mass, molecular mass, or combinations thereof. In certain embodiments, the detectable label is a fluorophore (i.e., a fluorescent label, fluorescent dye, etc.). Fluorophores of interest may include, but are not limited to, dyes suitable for use in analytical applications (e.g., flow cytometry, imaging, etc.).

In some instances, the fluorophore (i.e., dye) is a polymeric dye (e.g., a fluorescent polymeric dye). Fluorescent polymeric dyes that find use in the subject methods and systems are varied. In some instances of the method, the polymeric dye includes a conjugated polymer. Conjugated polymers (CPs) are characterized by a delocalized electronic structure which includes a backbone of alternating unsaturated bonds (e.g., double and/or triple bonds) and saturated (e.g., single bonds) bonds, where π-electrons can move from one bond to the other. As such, the conjugated backbone may impart an extended linear structure on the polymeric dye, with limited bond angles between repeat units of the polymer. For example, proteins and nucleic acids, although also polymeric, in some cases do not form extended-rod structures but rather fold into higher-order three-dimensional shapes. In addition, CPs may form "rigid-rod" polymer backbones and experience a limited twist (e.g., torsion) angle between monomer repeat units along the polymer backbone chain. In some instances, the polymeric dye includes a CP that has a rigid rod structure. The structural characteristics of the polymeric dyes can have an effect on the fluorescence properties of the molecules.

Any convenient polymeric dye may be utilized in the subject devices and methods. In some instances, a polymeric dye is a multi-chromophore that has a structure capable of harvesting light to amplify the fluorescent output of a fluorophore. In some instances, the polymeric dye is capable of harvesting light and efficiently converting it to emitted light at a longer wavelength. In some cases, the polymeric dye has a light-harvesting multi-chromophore system that can efficiently transfer energy to nearby luminescent species (e.g., a "signaling chromophore"). Mechanisms for energy transfer include, for example, resonant energy transfer (e.g., Forster (or fluorescence) resonance energy transfer, FRET), quantum charge exchange (Dexter energy transfer), and the like. In some instances, these energy transfer mechanisms are relatively short range; that is, close proximity of the light harvesting multi-chromophore system to the signaling chromophore provides for efficient energy transfer. Under conditions for efficient energy transfer, amplification of the emission from the signaling chromophore occurs when the number of individual chromophores in the light harvesting multi-chromophore system is large; that is, the emission from the signaling chromophore is more intense when the incident light (the "excitation light") is at a wavelength which is absorbed by the light harvesting multi-chromophore system than when the signaling chromophore is directly excited by the pump light.

The multi-chromophore may be a conjugated polymer. Conjugated polymers (CPs) are characterized by a delocalized electronic structure and can be used as highly responsive optical reporters for chemical and biological targets. Because the effective conjugation length is substantially shorter than the length of the polymer chain, the backbone contains a large number of conjugated segments in close proximity. Thus, conjugated polymers are efficient for light harvesting and enable optical amplification via Forster energy transfer.

Polymeric dyes of interest include, but are not limited to, those dyes described by Gaylord et al. in U.S. Publication Nos. 20040142344, 20080293164, 20080064042, 20100136702, 20110256549, 20110257374, 20120028828, 20120252986, 20130190193, 20160264737, 20160266131, 20180231530, 20180009990, 20180009989, and 20180163054, the disclosures of which are herein incorporated by reference in their entirety; and Gaylord et al., *J. Am. Chem. Soc.,* 2001, 123 (26), pp 6417-6418; Feng et al., *Chem. Soc. Rev.,* 2010,39, 2411-2419; and Traina et al., *J. Am. Chem. Soc.,* 2011, 133 (32), pp 12600-12607, the disclosures of which are herein incorporated by reference in their entirety.

In some embodiments, the polymeric dye includes a conjugated polymer including a plurality of first optically active units forming a conjugated system, having a first absorption wavelength (e.g., as described herein) at which the first optically active units absorb light to form an excited state. The conjugated polymer (CP) may be polycationic, polyanionic and/or a charge-neutral conjugated polymer.

The CPs may be water soluble for use in biological samples. Any convenient substituent groups may be included in the polymeric dyes to provide for increased water-solubility, such as a hydrophilic substituent group, e.g., a hydrophilic polymer, or a charged substituent group, e.g., groups that are positively or negatively charged in an aqueous solution, e.g., under physiological conditions. Any convenient water-soluble groups (WSGs) may be utilized in the subject light harvesting multi-chromophores. The term "water-soluble group" refers to a functional group that is well solvated in aqueous environments and that imparts improved water solubility to the molecules to which it is attached. In some embodiments, a WSG increases the solubility of the multi-chromophore in a predominantly aqueous solution (e.g., as described herein), as compared to a multichromophore which lacks the WSG. The water-soluble groups may be any convenient hydrophilic group that is well solvated in aqueous environments. In some cases, the hydrophilic water-soluble group is charged, e.g., positively or negatively charged. In certain cases, the hydrophilic water-soluble group is a neutral hydrophilic group. In some embodiments, the WSG is a hydrophilic polymer, e.g., a polyethylene glycol, a cellulose, a chitosan, or a derivative thereof.

As used herein, the terms "polyethylene oxide", "PEO", "polyethylene glycol" and "PEG" are used interchangeably and refer to a polymer including a chain described by the formula $—(CH_2—CH_2—O—)_n—$, or a derivative thereof. In some embodiments, "n" is 5000 or less, such as 1000 or less, 500 or less, 200 or less, 100 or less, 50 or less, 40 or less, 30 or less, 20 or less, 15 or less, such as 5 to 15, or 10 to 15. It is understood that the PEG polymer may be of any convenient length and may include a variety of terminal groups, including but not limited to, alkyl, aryl, hydroxyl, amino, acyl, acyloxy, and amido terminal groups. Functionalized PEGs that may be adapted for use in the subject multichromophores include those PEGs described by S. Zalipsky, "Functionalized poly(ethylene glycol) for preparation of biologically relevant conjugates", *Bioconjugate Chemistry* 1995, 6(2), 150-165. Water soluble groups of interest include, but are not limited to, carboxylate, phosphonate, phosphate, sulfonate, sulfate, sulfinate, ester, polyethylene glycols (PEG) and modified PEGs, hydroxyl, amine, ammonium, guanidinium, polyamine and sulfonium, polyalcohols, straight chain or cyclic saccharides, primary, secondary, tertiary, or quaternary amines and polyamines, phosphonate groups, phosphinate groups, ascorbate groups, glycols, including, polyethers, —COOM', —SO$_3$M', —PO$_3$M', —NR$_3$+, Y', (CH$_2$CH$_2$O)$_p$R and mixtures thereof, where Y' can be any halogen, sulfate, sulfonate, or oxygen containing anion, p can be 1 to 500, each R can be independently H or an alkyl (such as methyl) and M' can be a cationic counterion or hydrogen, —(CH$_2$CH$_2$O)$_{yy}$CH$_2$CH$_2$XR$^{yy}$, —(CH$_2$CH$_2$O)$_{yy}$CH$_2$CH$_2$X—, —X(CH$_2$CH$_2$O)$_{yy}$CH$_2$CH$_2$—, glycol, and polyethylene glycol, wherein yy is selected from 1 to 1000, X is selected from O, S, and NR$^{ZZ}$, and R$^{ZZ}$ and R$^{YY}$ are independently selected from H and C$_{1-3}$ alkyl.

The polymeric dye may have any convenient length. In some cases, the particular number of monomeric repeat units or segments of the polymeric dye may fall within the range of 2 to 500,000, such as 2 to 100,000, 2 to 30,000, 2 to 10,000, 2 to 3,000 or 2 to 1,000 units or segments, or such as 100 to 100,000, 200 to 100,000, or 500 to 50,000 units or segments.

The polymeric dyes may be of any convenient molecular weight (MW). In some cases, the MW of the polymeric dye may be expressed as an average molecular weight. In some instances, the polymeric dye has an average molecular weight of from 500 to 500,000, such as from 1,000 to 100,000, from 2,000 to 100,000, from 10,000 to 100,000 or even an average molecular weight of from 50,000 to 100,000. In certain embodiments, the polymeric dye has an average molecular weight of 70,000.

In certain instances, the polymeric dye includes the following structure:

where CP$_1$, CP$_2$, CP$_3$ and CP$_4$ are independently a conjugated polymer segment or an oligomeric structure, wherein one or more of CP$_1$, CP$_2$, CP$_3$ and CP$_4$ are bandgap-lowering n-conjugated repeat units, and each n and each m are independently 0 or an integer from 1 to 10,000 and p is an integer from 1 to 100,000.

In some instances, the polymeric dye includes the following structure:

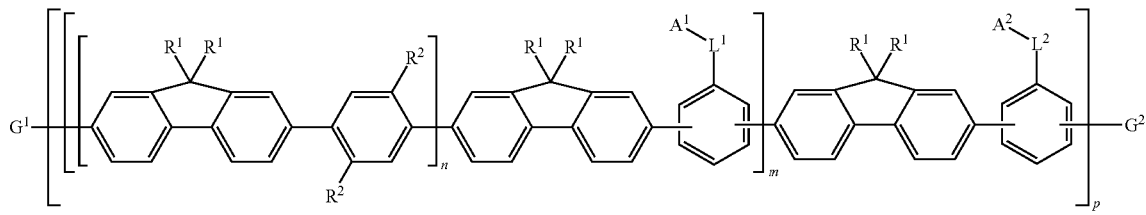

where each R$^1$ is independently a solubilizing group or a linker-dye; L$^1$ and L$^2$ are optional linkers; each R$^2$ is independently H or an aryl substituent; each A$^1$ and A$^2$ is independently H, an aryl substituent or a fluorophore; G$^1$ and G$^2$ are each independently selected from the group consisting of a terminal group, a π-conjugated segment, a linker and a linked specific binding member; each n and each m are independently 0 or an integer from 1 to 10,000; and p is an integer from 1 to 100,000. Solubilizing groups of interest include alkyl, aryl and heterocycle groups further substituted with a hydrophilic group such as a polyethylglycol (e.g., a PEG of 2-20 units), an ammonium, a sulphonium, a phosphonium, and the like.

In some cases, the polymeric dye includes, as part of the polymeric backbone, a conjugated segment having one of the following structures:

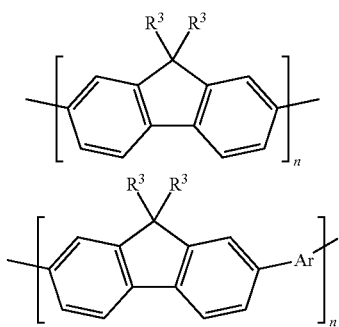

where each R$^3$ is independently an optionally substituted alkyl or aryl group; Ar is an optionally substituted aryl or heteroaryl group; and each n is an integer from 1 to 10,000.

In certain embodiments, R³ is an optionally substituted alkyl group. In certain embodiments, R³ is an optionally substituted aryl group. In some cases, R³ is substituted with a polyethyleneglycol, a dye, a chemoselective functional group or a specific binding moiety. In some cases, Ar is substituted with a polyethyleneglycol, a dye, a chemoselective functional group or a specific binding moiety.

In some instances, the polymeric dye includes the following structure:

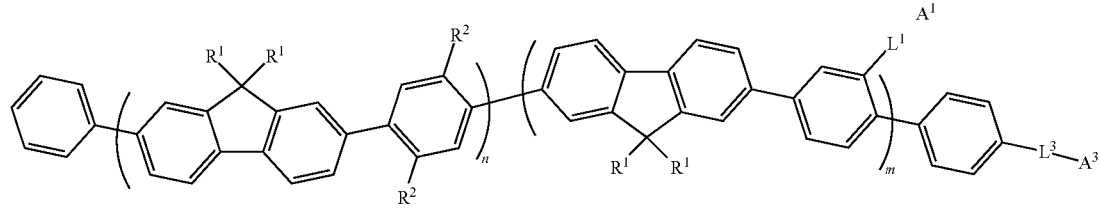

where each R¹ is independently a solubilizing group or a linker-dye group; each R² is independently H or an aryl substituent; each L¹ and L³ are independently optional linkers; each A¹ and A³ are independently H, a fluorophore, a functional group or a specific binding moiety (e.g., an antibody); and n and m are each independently 0 or an integer from 1 to 10,000, wherein n+m>1.

The polymeric dye may have one or more desirable spectroscopic properties, such as a particular absorption maximum wavelength, a particular emission maximum wavelength, extinction coefficient, quantum yield, and the like (see e.g., Chattopadhyay et al., "Brilliant violet fluorophores: A new class of ultrabright fluorescent compounds for immunofluorescence experiments." *Cytometry Part A*, 81A (6), 456-466, 2012).

In some embodiments, the polymeric dye has an absorption curve between 280 nm and 475 nm. In certain embodiments, the polymeric dye has an absorption maximum (excitation maximum) in the range 280 nm and 475 nm. In some embodiments, the polymeric dye absorbs incident light having a wavelength in the range between 280 nm and 475 nm.

In some embodiments, the polymeric dye has an emission maximum wavelength ranging from 400 nm to 850 nm, such as 415 nm to 800 nm, where specific examples of emission maxima of interest include, but are not limited to: 421 nm, 510 nm, 570 nm, 602 nm, 650 nm, 711 nm and 786 nm. In some instances, the polymeric dye has an emission maximum wavelength in a range selected from the group consisting of 410 nm to 430 nm, 500 nm to 520 nm, 560 nm to 580 nm, 590 nm to 610 nm, 640 nm to 660 nm, 700 nm to 720 nm, and 775 nm to 795 nm. In certain embodiments, the polymeric dye has an emission maximum wavelength of 421 nm. In some instances, the polymeric dye has an emission maximum wavelength of 510 nm. In some cases, the polymeric dye has an emission maximum wavelength of 570 nm. In certain embodiments, the polymeric dye has an emission maximum wavelength of 602 nm. In some instances, the polymeric dye has an emission maximum wavelength of 650 nm. In certain cases, the polymeric dye has an emission maximum wavelength of 711 nm. In some embodiments, the polymeric dye has an emission maximum wavelength of 786 nm. In certain instances, the polymeric dye has an emission maximum wavelength of 421 nm±5 nm. In some embodiments, the polymeric dye has an emission maximum wavelength of 510 nm±5 nm. In certain instances, the polymeric dye has an emission maximum wavelength of 570 nm±5 nm. In some instances, the polymeric dye has an emission maximum wavelength of 602 nm±5 nm. In some embodiments, the polymeric dye has an emission maximum wavelength of 650 nm±5 nm. In certain instances, the polymeric dye has an emission maximum wavelength of 711 nm±5 nm. In some cases, the polymeric dye has an emission maximum wavelength of 786 nm±5 nm. In certain embodiments, the polymeric dye has an emission maximum selected from the group consisting of 421 nm, 510 nm, 570 nm, 602 nm, 650 nm, 711 nm and 786 nm.

In some instances, the polymeric dye has an extinction coefficient of $1 \times 10^6$ $cm^{-1}M^{-1}$ or more, such as $2 \times 10^6$ $cm^{-1}M^{-1}$ or more, $2.5 \times 10^6$ $cm^{-1}M^{-1}$ or more, $3 \times 10^6$ $cm^{-1}M^{-1}$ or more, $4 \times 10^6$ $cm^{-1}M^{-1}$ or more, $5 \times 10^6$ $cm^{-1}M^{-1}$ or more, $6 \times 10^6$ $cm^{-1}M^{-1}$ or more, $7 \times 10^6$ $cm^{-1}M^{-1}$ or more, or $8 \times 10^6$ $cm^{-1}M^{-1}$ or more. In certain embodiments, the polymeric dye has a quantum yield of 0.05 or more, such as 0.1 or more, 0.15 or more, 0.2 or more, 0.25 or more, 0.3 or more, 0.35 or more, 0.4 or more, 0.45 or more, 0.5 or more, or even more. In certain cases, the polymeric dye has a quantum yield of 0.1 or more. In certain cases, the polymeric dye has a quantum yield of 0.3 or more. In certain cases, the polymeric dye has a quantum yield of 0.5 or more. In some embodiments, the polymeric dye has an extinction coefficient of $1 \times 10^6$ or more and a quantum yield of 0.3 or more. In some embodiments, the polymeric dye has an extinction coefficient of $2 \times 10^6$ or more and a quantum yield of 0.5 or more.

In certain embodiments, the dried dye composition includes other types of dye compositions, such as one or more non-polymeric dye compositions. As discussed above, dyes may include detectable moieties or markers that are detectable based on, for example, fluorescence emission maxima, fluorescence polarization, fluorescence lifetime, light scatter, mass, molecular mass, or combinations thereof. In certain embodiments, the non-polymeric dye includes a fluorophore (i.e., a fluorescent label, fluorescent dye, etc.). Fluorophores of interest may include but are not limited to dyes suitable for use in analytical applications (e.g., flow cytometry, imaging, etc.). A large number of non-polymeric dyes are commercially available from a variety of sources, such as, for example, Molecular Probes (Eugene, OR) and Exciton (Dayton, OH). For example, the fluorophore of the non-polymeric dye may be 4-acetamido-4'-isothiocyanatostilbene-2,2'disulfonic acid; acridine and derivatives such as acridine, acridine orange, acrindine yellow, acridine red, and acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate (Lucifer Yellow VS); N-(4-anilino-1-naphthyl)maleimide; anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanine and derivatives such as cyanosine, Cy3, Cy3.5, Cy5, Cy5.5, and Cy7; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylaminocoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein isothiocyanate (FITC), fluorescein chlorotriazinyl, naphthofluorescein, and QFITC (XRITC); fluorescamine; IR144; IR1446; Green Fluorescent Protein (GFP); Reef Coral Fluorescent Protein (RCFP); Lissamine™; Lissamine rhodamine, Lucifer yellow; Malachite Green isothiocyanate; 4-methylumbelliferone; ortho cresolphthalein; nitrotyrosine; pararosaniline; Nile Red; Oregon Green; Phenol Red; B-phycoerythrin (PE); o-phthaldialdehyde; pyrene and derivatives such as pyrene, pyrene butyrate and succinimidyl 1-pyrene butyrate; Reactive Red 4 (Cibacron™ Brilliant Red 3B-A); rhodamine and derivatives such as 6-carboxy-X-rhodamine (ROX), 6-carboxyrhodamine (R6G), 4,7-dichlororhodamine lissamine, rhodamine B sulfonyl chloride, rhodamine (Rhod), rhodamine B, rhodamine 123, rhodamine X isothiocyanate, sulforhodamine B, sulforhodamine 101, sulfonyl chloride derivative of sulforhodamine 101 (Texas Red), N,N,N',N'-tetramethyl-6-carboxyrhodamine (TAMRA), tetramethyl rhodamine, and tetramethyl rhodamine isothiocyanate (TRITC); riboflavin; rosolic acid and terbium chelate derivatives; xanthene; carotenoid-protein complexes, such as peridinin-chlorophyll proteins (PerCP); allophycocyanin (APC); or combinations thereof.

In some instances, the dye component of a given dried dye composition is a conjugate of a dye moiety and a specific binding member. The specific binding member and the dye moiety can be conjugated (e.g., covalently linked) to each other at any convenient locations of the two molecules, via an optional linker.

As used herein, the term "specific binding member" refers to one member of a pair of molecules which have binding specificity for one another. One member of the pair of molecules may have an area on its surface, or a cavity, which specifically binds to an area on the surface of, or a cavity in, the other member of the pair of molecules. Thus, the members of the pair have the property of binding specifically to each other to produce a binding complex. In some embodiments, the affinity between specific binding members in a binding complex is characterized by a $K_d$ (dissociation constant) of $10^{-6}$ M or less, such as $10^{-7}$ M or less, including $10^{-8}$ M or less, e.g., $10^{-9}$ M or less, $10^{-10}$ M or less, $10^{-11}$ M or less, $10^{-12}$ M or less, $10^{-13}$ M or less, $10^{-14}$ M or less, including $10^{-15}$ M or less. In some embodiments, the specific binding members specifically bind with high avidity. By high avidity is meant that the binding member specifically binds with an apparent affinity characterized by an apparent $K_d$ of $10 \times 10^{-9}$ M or less, such as $1 \times 10^{-9}$ M or less, $3 \times 10^{-10}$ M or less, $1 \times 10^{-10}$ M or less, $3 \times 10^{-11}$ M or less, $1 \times 10^{-11}$ M or less, $3 \times 10^{-12}$ M or less or $1 \times 10^{-12}$ M or less.

The specific binding member can be proteinaceous. As used herein, the term "proteinaceous" refers to a moiety that is composed of amino acid residues. A proteinaceous moiety can be a polypeptide. In certain cases, the proteinaceous specific binding member is an antibody. In certain embodiments, the proteinaceous specific binding member is an antibody fragment, e.g., a binding fragment of an antibody that specific binds to a polymeric dye. As used herein, the terms "antibody" and "antibody molecule" are used interchangeably and refer to a protein consisting of one or more polypeptides substantially encoded by all or part of the recognized immunoglobulin genes. The recognized immunoglobulin genes, for example in humans, include the kappa (k), lambda (l), and heavy chain genetic loci, which together comprise the myriad variable region genes, and the constant region genes mu (u), delta (d), gamma (g), sigma (e), and alpha (a) which encode the IgM, IgD, IgG, IgE, and IgA isotypes respectively. An immunoglobulin light or heavy chain variable region consists of a "framework" region (FR) interrupted by three hypervariable regions, also called "complementarity determining regions" or "CDRs". The extent of the framework region and CDRs have been precisely defined (see, "Sequences of Proteins of Immunological Interest," E. Kabat et al., U.S. Department of Health and Human Services, (1991)). The numbering of all antibody amino acid sequences discussed herein conforms to the Kabat system. The sequences of the framework regions of different light or heavy chains are relatively conserved within a species. The framework region of an antibody, that is the combined framework regions of the constituent light and heavy chains, serves to position and align the CDRs. The CDRs are primarily responsible for binding to an epitope of an antigen. The term antibody is meant to include full length antibodies and may refer to a natural antibody from any organism, an engineered antibody, or an antibody generated recombinantly for experimental, therapeutic, or other purposes as further defined below.

Antibody fragments of interest include, but are not limited to, Fab, Fab', F(ab')2, Fv, scFv, or other antigen-binding subsequences of antibodies, either produced by the modification of whole antibodies or those synthesized de novo using recombinant DNA technologies. Antibodies may be monoclonal or polyclonal and may have other specific activities on cells (e.g., antagonists, agonists, neutralizing, inhibitory, or stimulatory antibodies). It is understood that the antibodies may have additional conservative amino acid substitutions which have substantially no effect on antigen binding or other antibody functions.

In certain embodiments, the specific binding member is a Fab fragment, a $F(ab')_2$ fragment, a scFv, a diabody or a triabody. In certain embodiments, the specific binding member is an antibody. In some cases, the specific binding member is a murine antibody or binding fragment thereof. In certain instances, the specific binding member is a recombinant antibody or binding fragment thereof.

In certain embodiments, the dye compositions included in the dried reagent strainers include polymeric dye compositions, as described above. In some cases, the dye compositions included in the dried reagent strainers include non-polymeric dye compositions, as described above. In some instances, the dye compositions included in the dried reagent strainers include both polymeric dye compositions and non-polymeric dye compositions. As described above, the dried reagent strainers may include a plurality of dye compositions as described above, which dye compositions may be identical or distinct. For example, the strainers may include two or more, such as three or more, distinct dried polymeric dye compositions and two or more, such as three or more, or four or more, or five or more, distinct non-polymeric dye compositions. In some cases, the strainers include three or more distinct polymeric dye compositions and five or more distinct non-polymeric dye compositions.

As described above, the strainer may include both a polymeric dye composition and a non-polymeric dye composition. In some instances, a polymeric dye composition is mixed with a non-polymeric dye composition. In certain embodiments, the mixture of the polymeric dye composition and the non-polymeric dye composition do not undergo significant dye-dye interactions between the polymeric dye composition and the non-polymeric dye composition. For instance, the fluorescence emission energy of the polymeric dye composition is not significantly quenched by interactions with the non-polymeric dye composition. In some cases, the fluorescence emission energy of the polymeric dye composition is not significantly dissipated by a non-radiative transition. In these embodiments, the detectable fluorescence of the polymeric dye composition is not significantly less than would be expected as compared to the fluorescence of the polymeric dye composition in the absence of the non-polymeric dye composition. Similarly, in some embodiments, the fluorescence emission energy of the non-polymeric dye composition is not significantly quenched by interactions with the polymeric dye composition. For instance, the fluorescence emission energy of the non-polymeric dye composition may not be significantly dissipated by a non-radiative transition. In these embodiments, the detectable fluorescence of the non-polymeric dye composition is not significantly less than would be expected as compared to the fluorescence of the non-polymeric dye composition in the absence of the polymeric dye composition. In such instances, the polymeric and non-polymeric dyes of the mixed composition are stably associated with the same high surface area solid support, such that in these instances a given high surface area solid support includes two or more, such as three or more, including four or more different dyes, where in some instances only one of the dyes is a polymeric dye.

In certain embodiments, the dye composition includes a dye, such as a polymeric and/or non-polymeric dye, as described above. The dye composition may also include other components, such as, but not limited to a solvent, a buffer, a stabilizer, and the like. For example, the dye composition may include a stabilizer that reduces and/or substantially prevents degradation of the dye in the dye composition. In some cases, the presence of a stabilizer in the dye composition is sufficient to reduce and/or substantially prevent degradation of the dye in the dye composition for a certain period of time, such as 24 hours or more, or 48 hours or more, or 72 hours or more, or 4 days or more, or 5 days or more, or 6 days or more, or 1 week or more, or 2 weeks or more, or 3 weeks or more, or 4 weeks or more, or 2 months or more, or 3 months or more, or 4 months or more, or 5 months or more, or 6 months or more, or 9 months or more, or 1 year or more. Examples of stabilizers include, but are not limited to, bovine serum albumin (BSA), sodium azide, glycerol, phenylmethanesulfonyl fluoride (PMSF), and the like. Additional additives may also be present in the composition, such as, additives that preserve cells present in whole blood, e.g., platelet stabilizing factor, and the like. Examples of additives that may be included in the composition are anticoagulants such as ethylenediaminetetraacetic acid (EDTA), buffered citrate, heparin, and the like.

Embodiments of the cell strainers include a body that is configured to mate with an open end of a liquid container and includes an opening configured to allow passage of a liquid therethrough. Occupying at least a portion of, if not all of, the opening, is a filter that includes at least one dried reagent composition, e.g., as described above. When mated with an open end of a container, e.g., by placing the cell strainer onto an open end of a liquid container, the cell strainer is configured such that liquid passes through the opening of the body and the filter positioned therein to enter the liquid container. The shape of the body may vary as desired, where in some instances the shape is circular, ovoid, rectangular, triangular, etc., or even irregular. In some instances, the shape is circular, such that the body with the opening is an annular member where the center of the annular member is occupied by the filter. The dimensions of the opening of the body may vary, and in some instances the opening has a longest dimension, e.g., diameter, ranging from 1 to 50 mm, such as 2 to 30 mm, including 5 to 25 mm. The outer diameter of the body may vary, as desired, where in some instances the outer diameter of the body ranges from 1 to 50 mm, such as 2 to 30 mm including 5 to 25 mm. The cell strainer body may be produced from various materials, including plastics such as, for example, polystyrene (PS), polyvinylchloride (PVC), polycarbonate, glass, polyacrylate, polyacrylamide, polymethylmethacrylate (PMMA), polyethylene terephthalate (PET), polytetrafluorethylene (PTFE), thermoplastic polyurethane (TPU), silicone, polyethylene (PE) polypropylene (PP), polyvinyl alcohol (PVA) or compositions including one or more of the above-mentioned materials.

While the body of the cell strainer may vary, in some instances the cell strainer body includes: a) a flange to be held by an opening of a liquid container and defining an opening, b) a grip externally projecting from the flange; and c) a frame body provided below the flange, where the frame body is configured to hold the filter so that liquid passing through the opening passes through the filter into the liquid container and is therefore strained by the filter. Further details regarding cell strainer bodies, such as described above, are provided in U.S. Pat. Nos. 5,518,612; 5,593,587; and 10,046,257; the disclosures of which are herein incorporated by reference. In some instances, the cell strainer is a BD Falcon™ cell strainer, such as the 40μ, 70μ or 100μ mesh BD Falcon™ cell strainer (Becton Dickinson, Franklin Lakes, NJ), where the filter has been modified to include a dried reagent composition. An example of a cell strainer according to an embodiment of the invention is shown in FIG. 1. As shown in FIG. 1, cell strainer 1 has a flange 3 being held by the upper opening of a tube 2, a grip 4 externally projecting from said flange, a frame body 5 extending downward and housed in a tube below said flange, and a section holding said filter has a filter component 6 composed of nylon net having pore sizes ranging from 40 to 200 microns. The filter component includes one or more dried reagent compositions (Not shown), e.g., in the form of spots.

In some instances, the cell strainer is configured as a cap for a liquid container. Where the cell strainer is configured as a cap, the body, in addition to the opening and a filter present therein, may be configured to attach to the open end of a liquid container. While the cap may be configured to attach to the open end of a liquid container in a number of different ways, in some instances the cap is configured to snap fit or screw onto the open end of a liquid container. While the outer diameter of the cap may vary, in some instances the outer diameter of the body ranges 1 to 50 mm, such as 2 to 30 mm including 5 to 25 mm. In these embodiments, the cap may include a top portion, a bottom portion, an annular skirt extending from the top portion to the bottom portion and having an inner surface and an outer surface, and an orifice in the top portion that includes a filter, such as described above. The cap may further include an inner inverted skirt portion surrounded by the inner surface of the annular skirt. The compartment area extends from the top portion to an orifice at a bottom surface that includes a filter, such as described above. In some instances, the inner inverted skirt portion is separated from the inner surface of the annular skirt by an annular space. The inside surface of the annular skirt and the inner inverted skirt may each include at least one protrusion. The cap may further include a rim extending from the outer surface of the annular skirt. Further details regarding cell strainer caps that may be modified to include filters that include a dried reagent composition are provided in U.S. Pat. Nos. 5,601,728 and 5,711,875, the disclosures of which are herein incorporated by reference. In some instances, the cell strainer is a BD Falcon™ cap cell strainer, such as the 35μ mesh BD Falcon™ cap cell strainer (Becton Dickinson, Franklin Lakes, NJ), where the filter has been modified to include a dried reagent composition.

Figure 2:
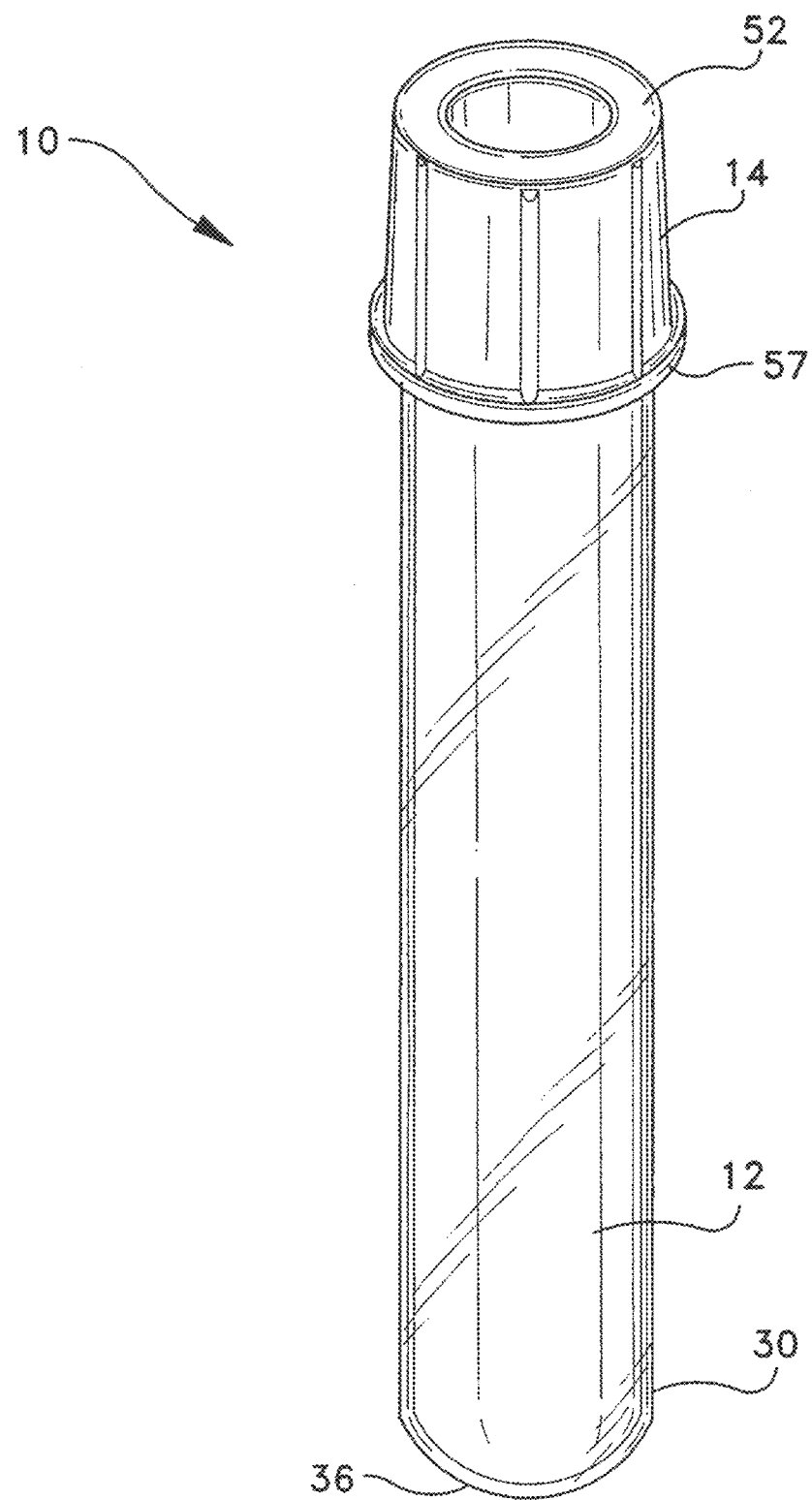
FIG. 2 is a perspective view of assembly illustrating strainer cap accordingly to any embodiment of the invention.
Figure 3:
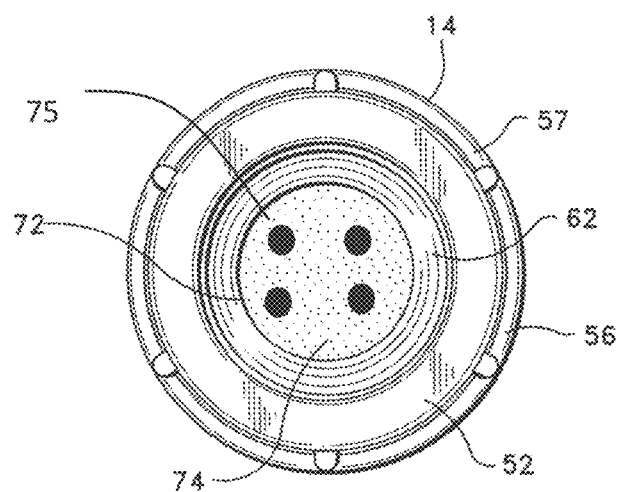
FIG. 3 is a top view of the cap of FIG. 2.
Figure 4:
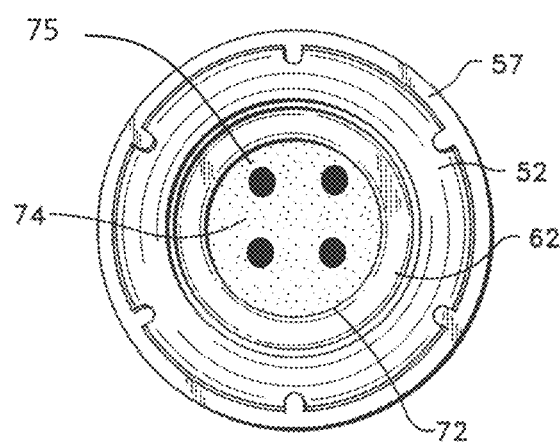
FIG. 4 is a bottom view of the cap of FIG. 2.

FIG. 2 illustrates a cell strainer assembly 10 that includes a liquid container 12 in the form of a tube, and a cell strainer cap or closure 14. The container may be made from impact resistant plastic or glass which is gas impermeable, optically clear, non-toxic and inert with respect to the suspension materials. Container 12 has a sidewall having an outer surface and an inner surface. The sidewall extends from an upper portion to a lower portion 30. Upper portion includes a top edge and an inner surface and lower portion 30 includes a rounded closed end 36. As shown in FIGS. 2, 3 and 4, cap 14 has a top surface 52, an annular outer skirt 56 extending from the top surface to the bottom stop ledge and a rim 57 extending from the annular skirt. Cap 14 further includes an inner annular inverted recessed skirt portion or cup 62 that extends from top surface 52. The sidewall of the cap decreases in circumference as it extends from the top surface to the bottom surface. The inverted recessed skirt portion defines a compartment area on the top surface of the cap for receiving a fluid sample. The inner wall surface of the annular outer skirt and the inner annular inverted recessed skirt are spaced from each other to define an annular space. The cap further includes an orifice 72 in the bottom surface of the inverted recessed skirt portion. A filter component 74 is attached to the orifice. The filter component includes one or more dried reagent spots 75. The orifice of the cap is sized and shaped to properly support the filtering of suspension into the container. The filter component 74 may be made from a nylon net material having a pore size of about 30 to about 200 microns. The filter mesh material is capable of removing impurities from samples such as supporting tissues, spiculae, or the like from a suspension containing lymphocytes as a large volume of filtrate to be processed is not absorbed by a filter mesh, as the filter mesh itself does not absorb water. The outer sidewall of inner annular skirt portion 62 includes a plurality of space protrusions for sealing against inner surface of upper portion of container 12. On the inner wall surface of skirt 56 of cap 14, a plurality of circumferential space protrusions are positioned to engage in snap-lock engagement with an annular sealing ring positioned on the upper portion of the container 12.

Figure 5:
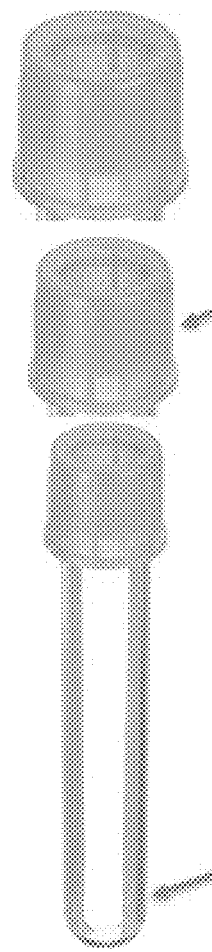
FIG. 5 provides a view of system of three stackable caps, according to an embodiment of the invention.

FIG. 5 provides a view of an embodiment of the invention in which multiple strainer caps, e.g., as described above, are employed. Specifically, as shown in FIG. 5, three stackable strainer caps are employed, where the caps are configured such that one cap may stack upon another cap so as to provide a common fluid flow path through sequentially through the filters of the stacked caps from the external environment to the interior of the container. In such configurations, each cap may include a distinct dried reagent composition(s), allowing a user to customize different reagents to be reconstituted in a container at the time of use. Methods of using such embodiments of the invention may include first determining which reagents, e.g., dyes, to employ in a given experiment, then selecting two or more stackable caps each containing one of the determined reagents to be employed, and placing the stackable caps on a container to a provide a device configured for use in the given experiment.

Figure 6:
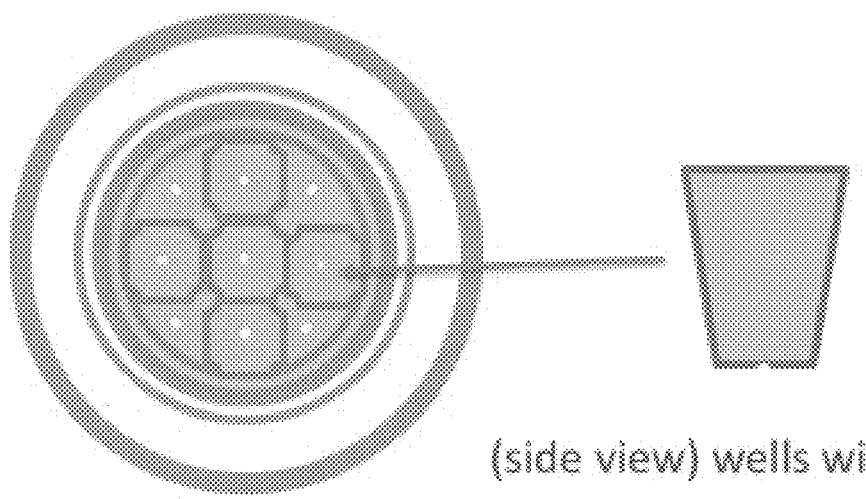
FIG. 6 provides a view of an alternative cap embodiment according to an embodiment of the invention.

While the above cap embodiment has been described in terms of a cell strainer cap that includes a filter, in some instances the cap has an alternative configuration, e.g., that includes one or more dried reagent compositions but lacks a filter component. Such caps may be referred to as dried reagent caps, where the cap is configured to mate with a liquid container, e.g., as described below, and includes one or more dried reagent compositions associated therewith such that when mated with a liquid container, a liquid may be flowed through the cap into the container and reconstitute the dried reagent(s). An example of such an alternative embodiment includes a cap defining one or more open bottomed wells and a dried reagent composition present in one or more of the open bottomed wells. Such cap configurations may have the same parameters as described above, e.g., in terms of size/shape/number of dried reagent compositions, etc., with the exception that the filter component is not present, such that the dried reagent composition(s) is associated with another structure of the cap, e.g., a well, a projection, a non-filtering frit, etc. In some instances, a cap is provided with one or more wells having one or more liquid passageways at the bottom thereof and including an amount of a dried reagent composition present therein. The number of wells in such dried reagent cap configurations may vary, ranging in some instances from 1 to 20, such as 1 to 10, e.g., 1 to 5. The volume of each well may also vary, ranging in some instances from 1 to 50 μL, such as 2 to 25 μL, including 2 to 15 μL. The wells are open bottomed, by which is meant that they included one or more liquid passageways (e.g., in the form of holes) at the bottom thereof. The diameter of a liquid passageway may vary, ranging in some instances from 10 to 1000μ, such as 50 to 500μ. FIG. 6 provides a view of such a cap according to an embodiment of the invention. As shown in FIG. 6, the cap is fabricated from polyethylene and includes multiple wells, where each well can hold up to 5-10 μL. Each well is open bottomed as each well includes a small hole(s) on the bottom. Reagent compositions are deposited into each well and dried individually. During use, a user may add a suitable quantity of liquid, e.g., 50-100 μL BSB buffer, to the cap to re-constitute all wells. Following reconstitution, the cap and container assembly may be centrifuged to collect reconstituted reagents to the bottom of the tube. In another embodiment, sample staining and/or lysis steps may be performed in the cap followed by the centrifugation of the entire volume of cell solution to the bottom of the tube. Performing sample staining in the cap instead of in the longer tube may prevent touching of the pipettor tips with samples or reagent to the side of the tube and causing unintended artifacts in stained cell samples. A given dried reagent composition is stably associated with the position of the cap where it is positioned. By stably associated is meant that during handling it does not move but is instead adhered to the position so that it remains at the position during handling. As such, the dried reagent composition is distinguished from a particle of a particle composition that merely touches a location but is not stably positioned, e.g., adhered to, the location.

As described above, cell strainers of the invention may be configured to mate with an open end of a liquid container. By "mate with" is meant that the cell strainer fits with or interacts with an open end of a liquid container such that liquid passes through the cell strainer in order to enter the liquid container. In mating with the open end of a liquid container, the cell strainer in some instances simply rests on the open end of a liquid container, such that the cell strainer can be easily removed from the liquid container through use of minimal force. In other instances, e.g., where the cell strainer is configured as a cap, e.g., as described above, the cell strainer may be configured such that some amount of force greater than minimal force must be used to separate the strainer from the container, such as where the strainer is configured to snap fit or screw onto the container.

The liquid container with which the cell strainer is configured to be employed may vary widely, depending on the particular embodiment and use for which it is configured. The size of the liquid container may. For instance, the container may have a volume (e.g., be configured to hold a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the container is configured to hold a volume (e.g., a volume of a liquid) ranging from 0.1 ml to 200 ml.

The shape of the container may also vary and may depend on the use of the dried dye reagent device. For example, as described herein, the dried dye reagent device may find use in an assay, such as an assay of a liquid sample (e.g., a biological sample). In these cases, the container may be configured in a shape that is compatible with the assay and/or the method or other devices used to perform the assay. For instance, the container may be configured in a shape of typical laboratory equipment used to perform the assay or in a shape that is compatible with other devices used to perform the assay.

In some embodiments, the container is a liquid container, such as a vial or a test tube. In certain cases, the liquid container is a vial. In certain cases, the liquid container is a test tube. As described above, the liquid container may be configured to hold a volume (e.g., a volume of a liquid). In embodiments where the liquid container is a vial or a test tube, the liquid container may be configured to hold a volume (e.g., a volume of a liquid) ranging from 0.1 ml to 1000 ml, such as from 0.5 ml to 900 ml, or 0.5 ml to 800 ml, or 0.5 ml to 700 ml, or 0.5 ml to 600 ml, or 0.5 ml to 500 ml, or 0.5 ml to 400 ml, or 0.5 ml to 300 ml, or 0.5 ml to 200 ml, or 0.5 ml to 100 ml, or 0.5 ml to 50 ml, or 0.5 ml to 25 ml, or 0.5 ml to 10 ml, or 0.5 ml to 5 ml, or 1 ml to 5 ml. In certain instances, the vial or test tube is configured to hold a volume (e.g., a volume of a liquid) ranging from 0.5 ml to 5 ml.

In other embodiments, the container is a well of a single well or a multi-well plate. Where the container is a well of a multi-well plate, the multi-well plate may include a plurality of liquid containers (e.g., wells), such as 2 or more, or 10 or more, or 50 or more, or 75 or more, or 100 or more, or 300 or more, or 500 or more, or 750 or more, or 1000 or more or 1500 or more, or 2000 or more liquid containers (e.g., wells). Examples of solid supports configured as multi-well plates may include, for example, 6, 12, 24, 96, 384 or 1536 liquid containers (e.g., wells). In embodiments where the liquid container is a well of a multi-well plate, an individual well may be configured to hold a volume (e.g., a volume of a liquid) ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the vial or test tube is configured to hold a volume (e.g., a volume of a liquid) ranging from 0.1 ml to 25 ml.

A container of the invention may also be configured as a bottle, cannister or analogous structure, e.g., configured to hold multiple dried dye compositions. In such instances the bottle, cannister or analogous structure may have a volume ranging from ranging from 0.1 ml to 1000 ml, such as from 0.1 ml to 900 ml, or 0.1 ml to 800 ml, or 0.1 ml to 700 ml, or 0.1 ml to 600 ml, or 0.1 ml to 500 ml, or 0.1 ml to 400 ml, or 0.1 ml to 300 ml, or 0.1 ml to 200 ml, or 0.1 ml to 100 ml, or 0.1 ml to 50 ml, or 0.1 ml to 25 ml, or 0.1 ml to 10 ml, or 0.1 ml to 5 ml, or 0.1 ml to 1 ml, or 0.1 ml to 0.5 ml. In certain instances, the vial or test tube is configured to hold a volume (e.g., a volume of a liquid) ranging from 0.1 ml to 25 ml.

Where desired, the container is fabricated from a material that is compatible with the liquid sample and/or reagent(s) or analyte(s) in contact with the multiplex dye device, e.g., during use. Examples of suitable container materials for the devices include, but are not limited to, glasses and plastics. For example, the container may be composed of a glass, such as, but not limited to, silicate glass, borosilicate glass, sodium borosilicate glass (e.g., PYREX™), fused quartz glass, fused silica glass, and the like. Other examples of suitable materials for the containers include polymeric materials, e.g., plastics, such as, but not limited to, polypropylene, polymethylpentene, polytetrafluoroethylene (PTFE), perfluoroethers (PFE), fluorinated ethylene propylene (FEP), perfluoroalkoxy alkanes (PFA), polyethylene terephthalate (PET), polyethylene (PE), polyetheretherketone (PEEK), and the like. The container may be clear or colored, e.g., amber, as desired, and in some instances may be configured to block transmission of light, i.e., it may be opaque.

In some instances, the liquid container is a Falcon™ tube, such as a Falcon™ conical tube or a Falcon™ round bottomed tube (Becton Dickinson, Franklin Lakes, NJ).

In some instances, the liquid container may include a dried reagent composition, such as a dried dye composition. In some instances, the liquid container has positioned therein one or more dried dye compositions that include one or more dyes stably associated with a high surface area solid support. In some instances, the one or more dried dye compositions are retained at a location of the container by a retainer, i.e., the dye compositions are stably associated with a given location or region of the container, e.g., a given location on the inner surface of the container. Any convenient retainer may be employed. In some instances the retainer is a mesh, where the mesh size may vary, ranging in some instances from 0.5 mm to 5 mm, The retainer may be fabricated from any suitable material, where materials of interest include, but are not limited to: glass materials (e.g., silicates), ceramic materials (e.g., calcium phosphates), metallic materials, and polymeric materials, etc. such as for example, polyethylene, polypropylene, polytetrafluoroethylene, polyvinylidine fluoride, and the like. Further details regarding such containers are provided in United States Patent Publication No. 20180224460, the disclosure of which is herein incorporated by reference. In certain embodiments, the container is one that includes one or more dried polymeric dye compositions distinctly positioned relative to an inner surface of the container. Further details regarding such containers are provided in United States Patent Publication No. 20170307600, the disclosure of which is herein incorporated by reference.

In certain embodiments, the container also includes a calibration standard. The calibration standard may be useful for determining the accuracy of the assay and for ensuring consistency between subsequent assays. In some cases, the calibration standard includes a labelled bead, such as a fluorescently labelled bead. The fluorescently labelled bead may be a standard fluorescently labeled bead that is typically used as a calibration standard. Examples of standard fluorescently labeled beads include, but are not limited to, fluorescently labelled microparticles or nanoparticles. In some cases, the fluorescently labeled beads are configured such that they remain suspended in the assay mixture and do not substantially settle or aggregate. In some embodiments, the fluorescently labeled beads include, but are not limited to, fluorescently labelled polystyrene beads, fluorescein beads, rhodamine beads, and other beads tagged with a fluorescent dye. Additional examples of fluorescently labeled beads are described in U.S. Pat. Nos. 6,350,619; 7,738,094; and 8,248,597, the disclosures of each of which are herein incorporated by reference in their entirety.

In some cases, the dried dye reagent cell strainers facilitate storage of the dye compositions for an extended period of time. For instance, a dried dye reagent device may be a storage stable device. In some cases, the dye compositions contained in the device are storage stable dye compositions, where the dye compositions are substantially stable for an extended period of time. By "stable" or "storage stable" or "substantially stable" is meant a dye composition that does not significantly degrade and/or lose activity over an extended period of time. For example, a storage stable dye composition may not have significant loss of fluorescence activity due to degradation of the dye composition over an extended period of time, such as 10% or less loss of fluorescence activity, or 9% or less, or 8% or less, or 7% or less, or 6% or less, or 5% or less, or 4% or less, or 3% or less, or 2% or less, or 1% or less loss of fluorescence activity over an extended period of time. In certain instances, a storage stable dye composition has 5% or less loss of fluorescence activity over an extended period of time. In some cases, a storage stable dye composition substantially retains its fluorescence activity over an extended period of time, such as retains 100% of its activity, or 99% or more, or 98% or more, or 97% or more, or 96% or more, or 95% or more, or 94% or more, or 93% or more, or 92% or more, or 91% or more, or 90% or more, or 85% or more, or 80% or more, or 75% or more of its activity over an extended period of time. For example, a storage stable dye composition may retain 90% or more of its fluorescence activity over an extended period of time. In some cases, a storage stable composition retains 95% or more of its fluorescence activity over an extended period of time. An extended period of time is a period of time such as 1 week or more, or 2 weeks or more, or 3 weeks or more, or 1 month or more, or 2 months or more, or 3 months or more, or 4 months or more, or 6 months or more, or 9 months or more, or 1 year or more, or 1.5 years (e.g., 18 months) or more, or 2 years or more, or 2.5 years (e.g., 30 months) or more, or 3 years or more, or 3.5 years (e.g., 42 months) or more, or 4 years or more, or 4.5 years (e.g., 54 months) or more, or 5 years or more. For instance, an extended period of time may be 6 months or more. In some cases, an extended period of time is 9 months or more. In some cases, an extended period of time is 1 year (e.g., 12 months) or more. In some cases, an extended period of time is 1.5 years (e.g., 18 months) or more. In some cases, an extended period of time is 2 years (e.g., 24 months) or more. In some instances, the extended period of time is 10 years or less, such as 7.5 years or less, including 5 years or less, e.g., 2 years or less.

Where desired, the strainers may include a cover, e.g., configured to mate with the body opening, which further protects the dried dye composition(s) of the filter from the external environment. In some instances, the cover is fabricated from an opaque material, e.g., a black material, where suitable materials include those described in U.S. Pat. No. 6,686,004, the disclosure of which is herein incorporated by reference.

METHODS OF USE

Aspects of the present disclosure also include methods of using the subject dried reagent cell strainers. As described above, a dried reagent strainer of the invention may include a cell strainer having a filter that includes one or more dried reagent, e.g., dye, compositions. In some instances, the method of using the cell strainer includes reconstituting the reagent composition. In certain embodiments, the method includes passing a volume of a liquid through the filter of the cell strainer in a manner sufficient to produce a reconstituted reagent composition. The volume of liquid may be passed through the filter of the strainer, and subsequently into a liquid container mated with the cell strainer, using any convenient liquid handling apparatus, such as, but not limited to, syringes, needles, pipets, aspirators, among other liquid handling devices. In some instance a volume of liquid, e.g., ranging from 5 to 500 μl, such as 10 to 250 μl, e.g., 10 to 100 μl, is introduced into a receiving portion of the cell strainer, and where desired force may be applied to urge the liquid through the strainer to thereby reconstitute the dried reagent(s), where the force may vary, such as suction force, centrifuge force, etc., as desired.

In certain embodiments, the liquid includes a biological sample. In some cases, the biological sample may be derived from specific biological fluids, such as, but not limited to, blood, mucus, lymphatic fluid, synovial fluid, cerebrospinal fluid, saliva, bronchoalveolar lavage, amniotic fluid, amniotic cord blood, urine, vaginal fluid and semen. In some embodiments, the biological sample includes whole blood or a fraction thereof. In some embodiments, the biological sample includes blood plasma.

In certain embodiments, the method also includes mixing the contents of the liquid container after passing the volume of liquid through the filter and into the inside the liquid container. The mixing may be performed using any convenient protocol. For example, the mixing may be performed using an agitator. The agitator may be any convenient agitator sufficient for mixing the liquid inside the liquid container, including, but not limited to, vortexers, sonicators, shakers (e.g., manual, mechanical, or electrically powered shakers), rockers, oscillating plates, magnetic stirrers, static mixers, rotators, blenders, mixers, tumblers, orbital shakers, among other agitating protocols.

In some cases, the method also includes assaying the reconstituted reagent composition (where in this context the reconstituted reagent composition may further include one or more reaction products, e.g., labeled cells, etc.). In such instances, the methods may include removing an amount or volume of the reconstituted reagent composition from the container, e.g., for assaying. Assaying the reconstituted reagent composition may be performed using any suitable assay apparatus. For example, the assay apparatus may be a flow cytometer. In these embodiments, the assaying includes flow cytometrically analyzing the reconstituted dye composition. In some instances, the assaying includes contacting the reconstituted reagent composition with electromagnetic radiation (e.g., light), such as electromagnetic radiation having a wavelength that corresponds to the excitation maxima of the reconstituted dye composition. The assaying may further include detecting emitted light from the excited dye compositions. For instance, the method may include detecting emitted light from the excited dye compositions at one or more wavelengths that correspond to the emission maxima of the dye compositions.

Suitable flow cytometry systems and methods for analyzing samples that may be employed in methods of the invention include, but are not limited to those described in Ormerod (ed.), *Flow Cytometry: A Practical Approach*, Oxford Univ. Press (1997); Jaroszeski et al. (eds.), *Flow Cytometry Protocols*, Methods in Molecular Biology No. 91, Humana Press (1997); *Practical Flow Cytometry*, 3rd ed., Wiley-Liss (1995); Virgo, et al. (2012) *Ann Clin Biochem.* January; 49(pt 1):17-28; Linden, et. al., *Semin Throm Hemost.* 2004 October; 30(5):502-11; Alison, et al. *J Pathol*, 2010 December; 222(4):335-344; and Herbig, et al. (2007) *Crit Rev Ther Drug Carrier Syst.* 24(3):203-255; the disclosures of which are incorporated herein by reference. In certain instances, flow cytometry systems of interest include BD Biosciences FACSCanto™ II flow cytometer, BD Accuri™ flow cytometer, BD Biosciences FACSCelesta™ flow cytometer, BD Biosciences FACSLyric™ flow cytometer, BD Biosciences FACSVerse™ flow cytometer, BD Biosciences FACSymphony™ flow cytometer BD Biosciences LSRFortessa™ flow cytometer, BD Biosciences LSR-Fortess™ X-20 flow cytometer and BD Biosciences FACSCalibur™ cell sorter, a BD Biosciences FACSCount™ cell sorter, BD Biosciences FACSLyric™ cell sorter and BD Biosciences Via™ cell sorter BD Biosciences Influx™ cell sorter, BD Biosciences Jazz™ cell sorter, BD Biosciences Aria™ cell sorters and BD Biosciences FACSMelody™ cell sorter, or the like. In some embodiments, the subject particle sorting systems are flow cytometric systems, such those described in U.S. Pat. Nos. 9,952,076; 9,933,341; 9,726,527; 9,453,789; 9,200,334; 9,097,640; 9,095,494; 9,092,034; 8,975,595; 8,753,573; 8,233,146; 8,140,300; 7,544,326; 7,201,875; 7,129,505; 6,821,740; 6,813,017; 6,809,804; 6,372,506; 5,700,692; 5,643,796; 5,627,040; 5,620,842; 5,602,039; the disclosure of which are herein incorporated by reference in their entirety.

Other methods of analysis may also be used, such as, but not limited to, liquid chromatography-mass spectrometry or gas chromatography-mass spectrometry systems. For example, assaying may include the use of an analytical separation device such as a liquid chromatograph (LC), including a high-performance liquid chromatograph (HPLC), a micro- or nano-liquid chromatograph or an ultra-high pressure liquid chromatograph (UHPLC) device, a capillary electrophoresis (CE), or a capillary electrophoresis chromatograph (CEC) apparatus. Mass spectrometer (MS) systems may also be used to assay the dye compositions. Examples of mass spectrometers may include, but are not limited, to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof. Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof.

In certain embodiments, the device is included in an apparatus that is fully automated. By "fully automated" is meant that the apparatus receives a reagent device and prepares a reconstituted dye composition with little to no human intervention or manual input into the subject systems. In certain embodiments, the subject systems are configured to prepare and analyze the reconstituted dye composition without any human intervention.

In certain embodiments, the method also includes storing the reconstituted reagent composition for a period of time. The reconstituted reagent composition may be stored for a period of time before, during and/or after assaying the reconstituted dye composition. In some instances, the reconstituted reagent composition is stored for a period of time such as 24 hours or more, or 48 hours or more, or 72 hours or more, or 4 days or more, or 5 days or more, or 6 days or more, or 1 week or more, or 2 weeks or more, or 3 weeks or more, or 4 weeks or more, or 2 months or more, or 3 months or more, or 4 months or more, or 5 months or more, or 6 months or more, or 9 months or more, or 1 year or more. In certain cases, the reconstituted reagent composition is stored for 24 hours or more. In certain cases, the reconstituted reagent composition is stored for 48 hours or more. In certain cases, the reconstituted reagent composition is stored for 72 hours or more. In certain cases, the reconstituted reagent composition is stored for 1 week or more. In certain cases, the reconstituted reagent composition is stored for 2 weeks or more. In certain cases, the reconstituted reagent composition is stored for 3 weeks or more.

Embodiments of the method may further include shipping the reconstituted reagent composition to a remote location. A "remote location," is a location other than the location at which the dye composition is reconstituted. For example, a remote location could be another location (e.g., office, lab, etc.) in the same city, another location in a different city, another location in a different state, another location in a different country, etc. As such, when one item is indicated as being "remote" from another, what is meant is that the two items can be in the same room but separated, or at least in different rooms or different buildings, and can be at least one mile, ten miles, or one hundred miles or more apart.

METHODS OF MAKING

Aspects of the present disclosure also include methods of making a dried reagent cell strainer as described herein. In certain embodiments, the methods of making include producing a filter that includes one or more dried reagent compositions, e.g., by positioning one or more dried reagent compositions on a surface of a filter of cell strainer. For example, the methods of making may include positioning one or more dried dye compositions (e.g., first and second dried dye compositions) on a surface if a filer of a cell strainer, such as on a bottom surface of a filter of a cell strainer and/or a top surface of a filter of a cell strainer. The dried reagent compositions may be positioned on the surface of filter (or in a well such as in the embodiments shown in FIG. 6) using any convenient protocol, such as, but not limited to, spraying, printing, or other deposition method.

In certain embodiments, the reagent composition is positioned on the surface of the filter first and then the deposited composition is dried to provide a dried reagent composition on the surface of the filter. In these embodiments, the reagent composition may be provided as a liquid reagent composition and the liquid reagent composition may be distinctly positioned on the surface of the filter. The distinctly positioned liquid reagent composition may be dried to provide a distinctly positioned dried reagent composition on the surface of the filter. The liquid reagent composition may be distinctly positioned on the surface of the filter using any convenient liquid handling apparatus, such as, but not limited to, syringes, needles, pipets, aspirators, among other liquid handling devices. In some instances, the liquid reagent composition may be distinctly positioned on the surface of the filter using a printer, such as, but not limited to, an inkjet printer. A liquid reagent composition that is distinctly positioned on the surface of the filter may be dried using any convenient drying protocol. In some cases, the filter may be heated or placed in an environment at a temperature greater than standard conditions. In certain instances, the temperature is a temperature greater than standard conditions that is sufficient to dry the liquid dye composition, but less than a temperature that would cause degradation to the dye composition. For example, the solid support may be heated to a temperature ranging from 30° C. to 50° C., such as 30° C. to 45° C. to provide a dried reagent composition. In certain embodiments, the temperature is applied to the solid support for a time sufficient to dry the dye composition, such as 1 min or more, or 5 min or more, or 10 min or more, or 15 min or more, or 20 min or more, or 30 min or more. In embodiments that include two or more reagent compositions on the surface of the filter, the different reagent compositions may be positioned and dried on the surface of the filter sequentially, or each reagent composition may be positioned on the surface of the filter and all of the reagent compositions may be dried simultaneously.

As described herein, the dry reagent cell strainer may include two or more reagent compositions (e.g., polymeric dye compositions) distinctly positioned on a surface of a filter. As such, in some cases, the method includes positioning the reagent compositions at separate locations on the surface of the filter. For example, the method may include positioning first and second polymeric dye compositions at separate locations on the surface of the filter. Additional reagent, e.g., dye, compositions may be provided on the surface of the filter, such as a third polymeric dye composition. In these embodiments, the method may further include distinctly positioning the third reagent, e.g., polymeric dye, composition on the surface of the filter. Additional polymeric and/or non-polymeric dye compositions may also be distinctly positioned on the surface of the filter, as desired.

KITS

Aspects of the disclosure also include kits that include a dried reagent cell strainer, e.g., as described herein. In certain embodiments, the kit includes one or more dried reagent cell strainers, e.g., as described herein. Kits of interest may also include a container, e.g., as described herein. In addition, the kits may include packaging configured to hold the dried reagent cell strainer, container, etc. The packaging may be a sealed packaging, e.g., a water vapor-resistant container, optionally under an air-tight and/or vacuum seal. In certain instances, the packaging is a sterile packaging, configured to maintain the device enclosed in the packaging in a sterile environment. By "sterile" is meant that there are substantially no microbes (such as fungi, bacteria, viruses, spore forms, etc.). The kits may further include a liquid container, e.g., as described above.

The kits may further include a buffer. For instance, the kit may include a buffer, such as a sample buffer, a wash buffer, an assay buffer, and the like. The kits may further include additional reagents, such as but not limited to, detectable labels (e.g., fluorescent labels, colorimetric labels, chemiluminescent labels, multicolor reagents, avidin-streptavidin associated detection reagents, radiolabels, gold particles, magnetic labels, etc.), and the like. In certain embodiments, the kits may also include a calibration standard. For example, the kits may include a set of labelled beads, such as a set of standard fluorescently labelled beads.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another means would be a computer readable medium, e.g., CD, DVD, Blu-Ray, computer-readable memory (e.g., flash memory), etc., on which the information has been recorded or stored. Yet another form that may be present is a website address which may be used via the Internet to access the information at a removed site. Any convenient form of instructions may be present in the kits.

UTILITY

The subject devices and methods find use in applications where cell analysis from a biological sample may be desired for research, laboratory testing or for use in therapy. In some embodiments, the subject devices and methods facilitate analysis of cells obtained from fluidic or tissue samples such as specimens for diseases, including but not limited to cancer. Devices and methods of the present disclosure also allow for analyzing cells from a biological sample (e.g., organ, tissue, tissue fragment, fluid) with enhanced efficiency and low cost.

The subject devices and methods find use in applications where the analysis of a sample using two or more dye compositions is desired. For example, the subject devices and methods find use in applications where the analysis of a sample using two or more dye compositions is desired, such as two or more polymeric dye compositions. Embodiments of the subject devices and methods also find use in applications where analysis of a sample using two or more polymeric dye compositions in combination with one or more non-polymeric dye compositions is desired. Thus, the subject devices and methods find use in applications where a sample is analyzed for two or more analytes of interest using two or more corresponding dye compositions. In some cases, where non-polymeric dye compositions are also included in the reagent devices, the subject devices and methods find use in applications where a sample is analyzed for two or more analytes of interest using two or more corresponding polymeric dye compositions and non-polymeric dye compositions.

The subject reagent devices and methods find use in applications where a minimization in dye-dye interactions is desired. As described herein, the subject reagent devices and methods provide two or more distinct dried polymeric dye compositions, where each dye composition includes a dye stably associated with high surface area solid support, facilitating a minimization in dye-dye interactions. A minimization in dye-dye interactions may facilitate the collection of more precise and/or accurate data with respect to the assays performed using the subject reagent devices. For instance, the subject reagent devices and methods may facilitate a reduction in dye-dye interactions as compared to reagent devices in which two or more dye compositions are provided but are not stably associated with different high surface area solid supports.

The devices and methods described herein find use in applications where a panel of analytes in sample is to be assayed. Where desired, the devices and methods may be used in customized panel assays, where a user may specify the analytes of a panel of interest and reagent device with dyes selected for the panel prepare on a custom basis. The dyes of the panel may be present in separate dried dye compositions, or two or more of the dyes for the panel may be combined in a single dried dye composition, e.g., as described above.

As can be appreciated from the disclosure provided above, embodiments of the present disclosure have a wide variety of applications. Accordingly, the examples presented herein are offered for illustration purposes and are not intended to be construed as a limitation on the embodiments of the present disclosure in any way. Those of ordinary skill in the art will readily recognize a variety of noncritical parameters that could be changed or modified to yield essentially similar results. Thus, the following examples are put forth so as to provide those of ordinary skill in the art with a complete disclosure and description of how to make and use embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

EXAMPLES

I. Demonstrate the Utility of flowCAP™ Tube Design in the Deposition of Reagent Spots, Drying and Applications in Flow Cytometry A. Experiment:
1. Reagent Preparation:

| | | | | | | | Deposition Solution | | | |
|---|---|---|---|---|---|---|---|---|---|---|
| | | | | | | | BD bulk reagents | | | |
| Marker | Clone | Fluorochrome | Bulk (mg/mL) | ug/test | Deposition volume (uL) | Deposition concentration (mg/mL) | Bulk volume (uL) | 4X buffer (uL) | DI water (uL) | Total volume (uL) |
| CD4 | SK3 | BV421 | 0.2 | 0.15 | 1 | 0.15 | 15 | 5 | 0 | 20 |
| CD8 | SK1 | BV510 | 0.2 | 0.15 | 1 | 0.15 | 15 | 5 | 0 | 20 |
| CD3 | UCHT-1 | BB700 | 0.58 | 0.15 | 1 | 0.15 | 5.2 | 5 | 9.8 | 20 |
| CD19 | | BV605 | 0.2 | 0.15 | 1 | 0.15 | 15 | 5 | 0 | 20 |
| OFF-shelf product | | | | | | | | | | |
| CD45 | | FITC | BD Catlog#340664 (lot #7173705) | | | | | | | |

Deposition solutions for four Sirigen dye conjugates were prepared from bulk solution with 4×BD drying matrix buffer according to the table above. An off-shelf reagent, CD45-FITC, was also used in the assay in liquid form.

2. Preparation of FlowCAP Tubes with Dried Reagent Spots:

The blue cap from Falcon™ tube with cell strainer cap (Corning catalog #352235) was removed and placed upside down on a lab bench. A volume of 1 μL of each of the four deposition solutions was deposited on the cap cell strainer mesh on the cap at separate locations, forming a 4-spot array.

The deposited reagent spots were dried by placing the cap into a 37° C. oven for 10 min. The cap was placed back to the tube and the tube was placed into an alumina pouch with a desiccant. The pouch was heat-sealed and placed at room temperature overnight before use.

Figure 7A:
FIGS. 7A to 7C provide various views of a Flow-CAP tube prepared with dried reagent compositions on the filter thereof, as described in greater detail in the experimental section below.
Figure 7B:
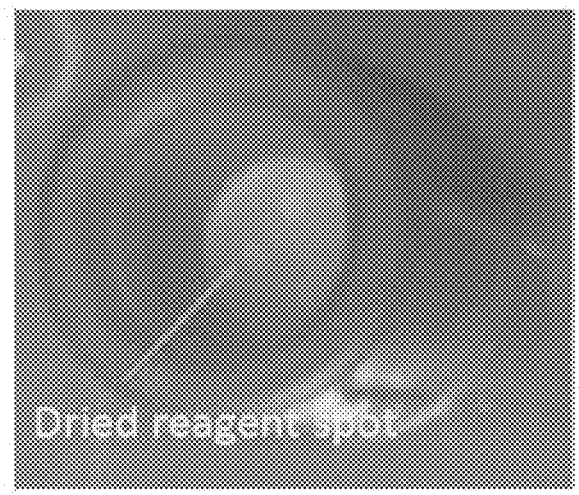
Figure 7C:
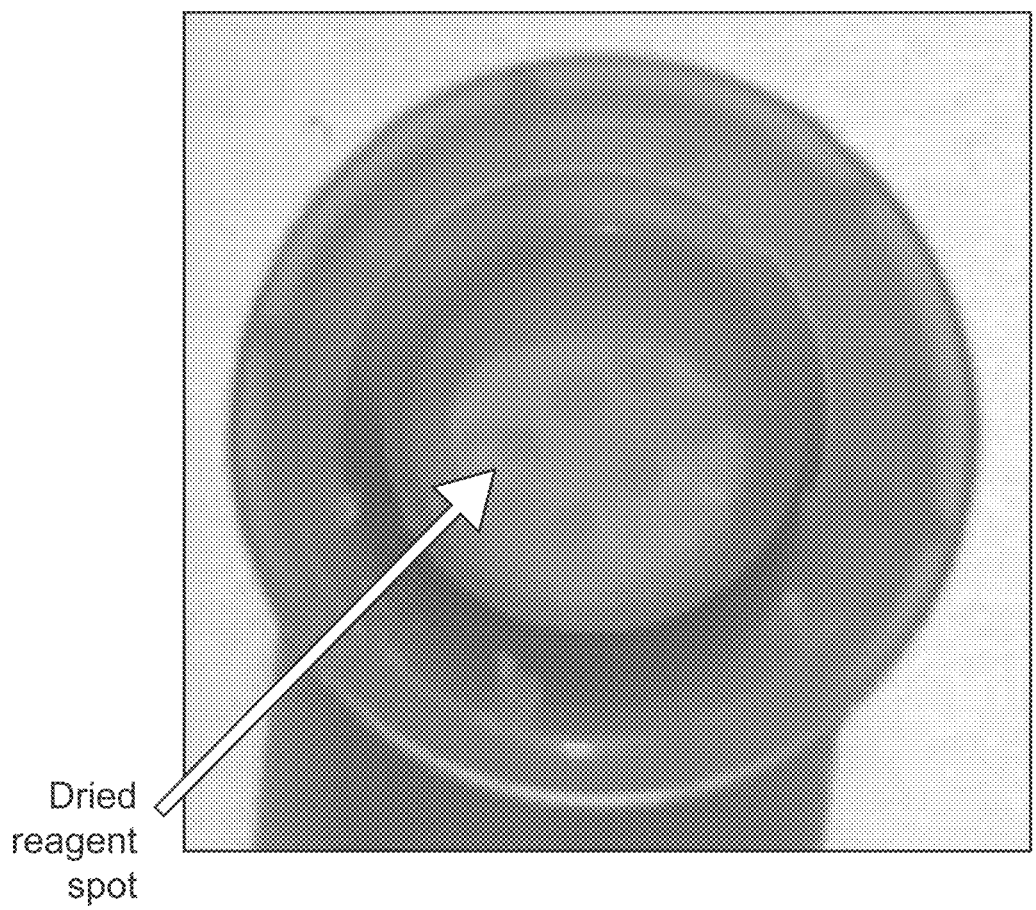

FIGS. 7A to 7C provide pictures of the produced cap from different perspectives.

3. Flow Cytometer Analysis with FlowCAP Tubes.

Prior to the assay, FlowCAP tubes were taken out of the alumina pouch and a volume of 10 μL of CD45-FITC was placed on the bottom of the tube. A volume of 100 μL of brilliant stain buffer (BSB) was added to the cap of the FlowCAP tube and allowed to incubate at room temperature for 5 min to re-constitute the dried reagents. The tube was then centrifuged at 300×g for 1 min to collect all the reconstituted reagent solution to the bottom of the tube.

For the positive control tube, a volume of 100 μL of the BSB buffer was added to a regular 5-mL polystyrene tube without cap, and 10 μL of CD45-FITC was added to the tube, followed by 1 μL of each of the prepared deposition solution for each of Sirigen dye.

For cell staining, a volume of 50 μL of whole blood was added to each tube, and mixed with the reagent solution. The tube was incubated at room temperature and protected from light for 30 minutes. A volume of 900 μL of 1×FACSLyse buffer was added to each tube and incubated for 15 minutes. The tube was centrifuged at room temperature at 300×g for 5 min. After the supernatant was removed, a volume of 2 mL of wash buffer (PBS/BSA/NaN$_3$) was added and cells are re-suspended. The tube was centrifuged at room temperature at 300×g for 5 min and the supernatant was removed. Finally, the cells were re-suspended into 500 μL of the wash buffer and the tube was keep in dark prior to analysis on FACSLyric.

Standard flow cytometer procedure was followed for the analysis of samples on FACSLyric. Compensation values were manually adjusted.

B. Results

Figure 8:
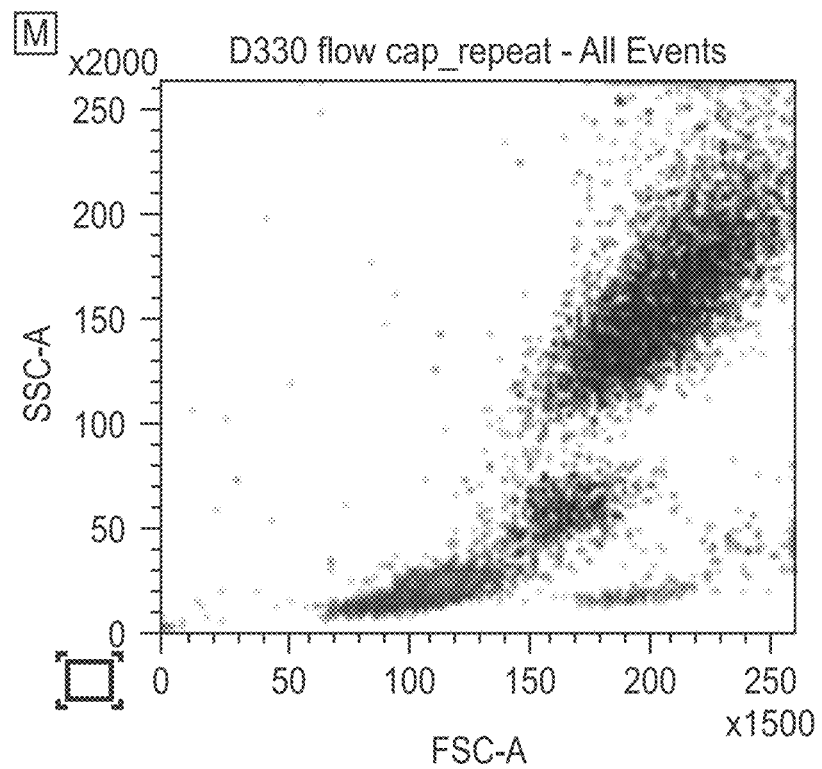
FIG. 8 provides data obtained from Flow-CAP tube with dried reagent spots according to an embodiment of the invention, as described in greater detail in the Experimental section, below.
Figure 8:
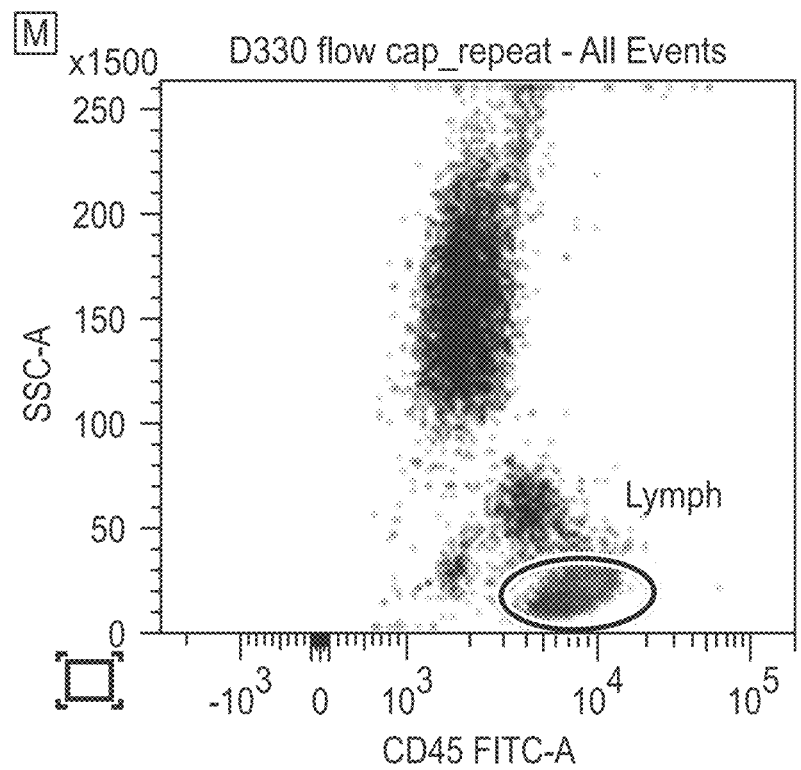
Figure 8:
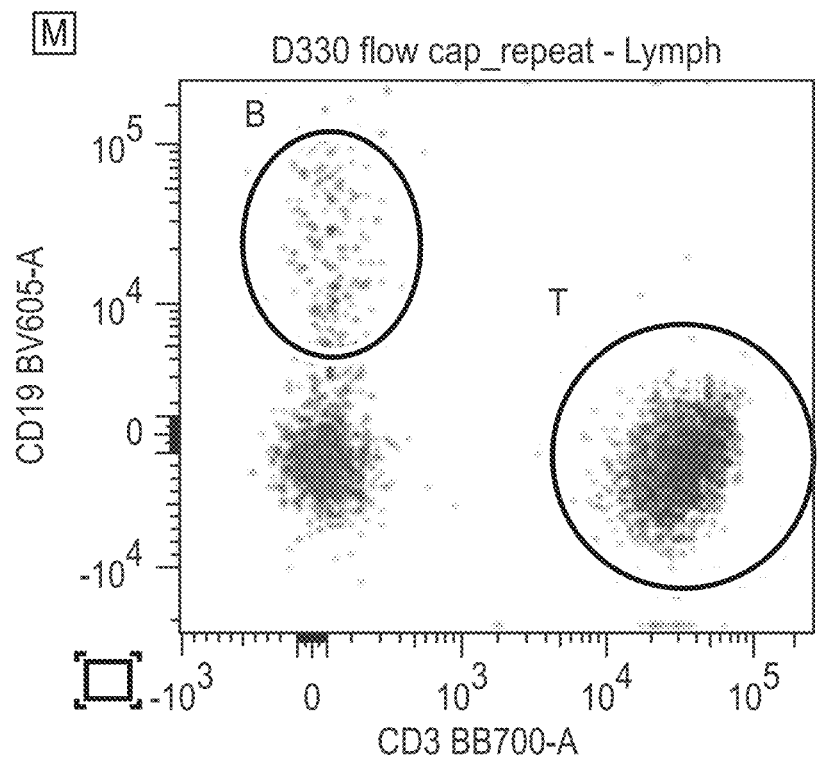
Figure 8:
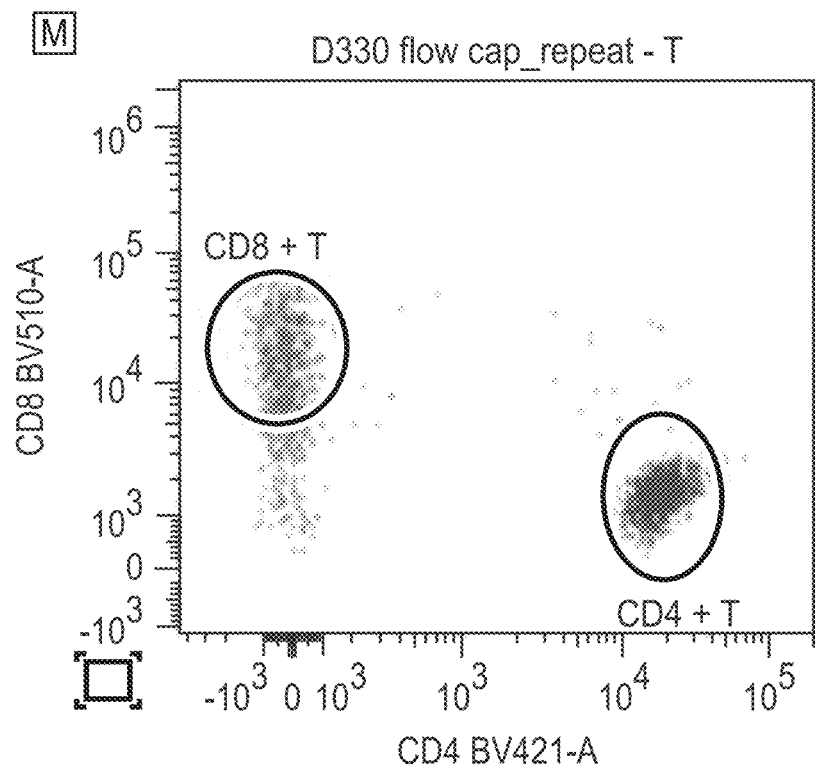
Figure 8:
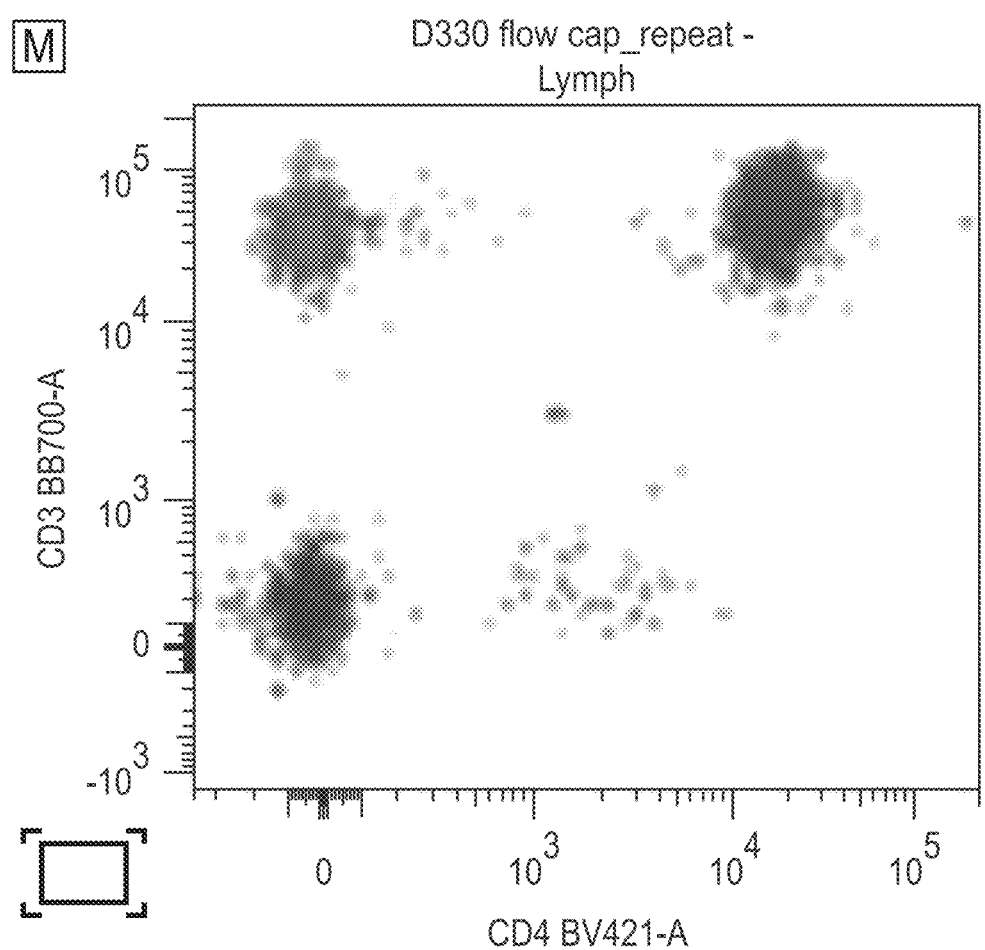
Figure 9:
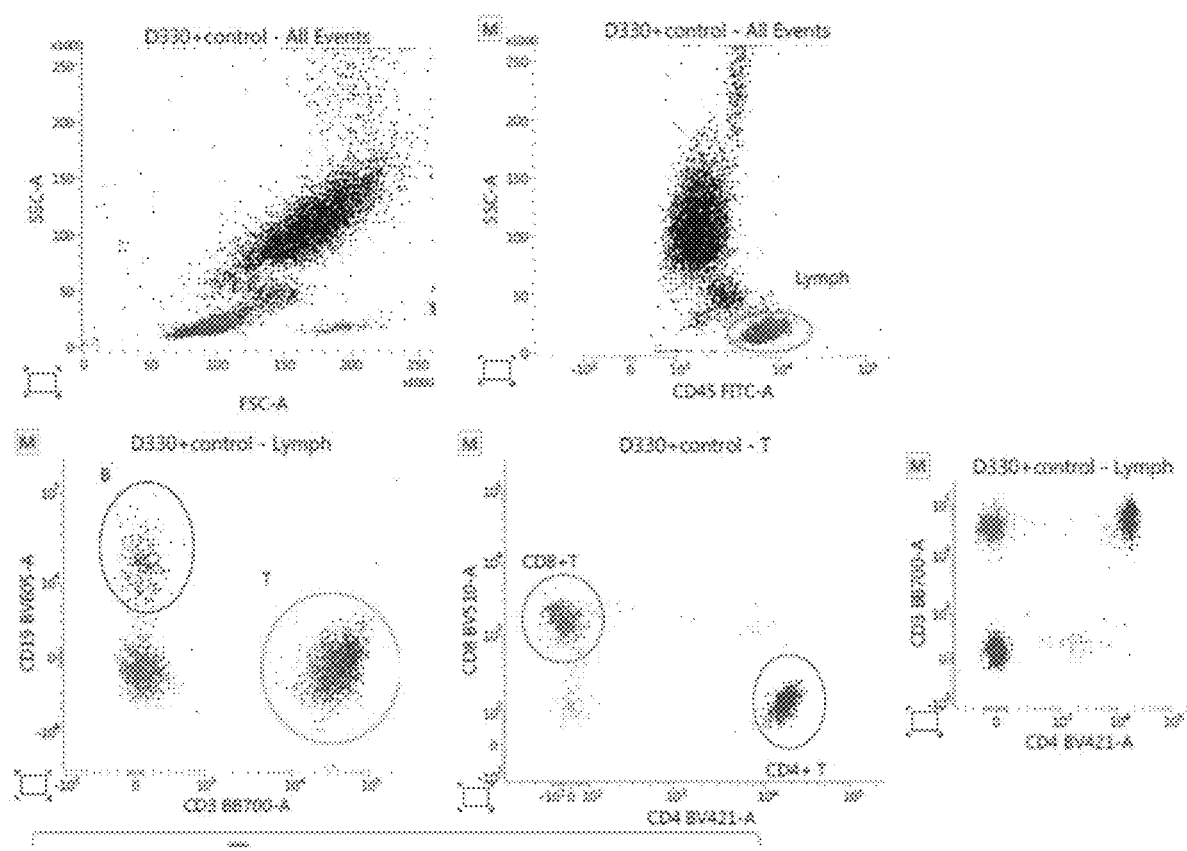
FIG. 9 provides data obtained by adding individual reagent in liquid form to a tube in a control experiment, as described in greater detail in the Experimental section, below.
Figure 10A:
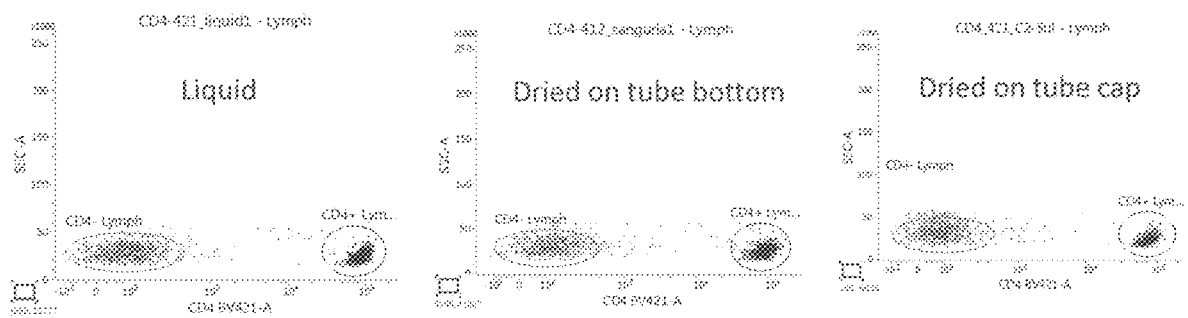
Figure 10B:
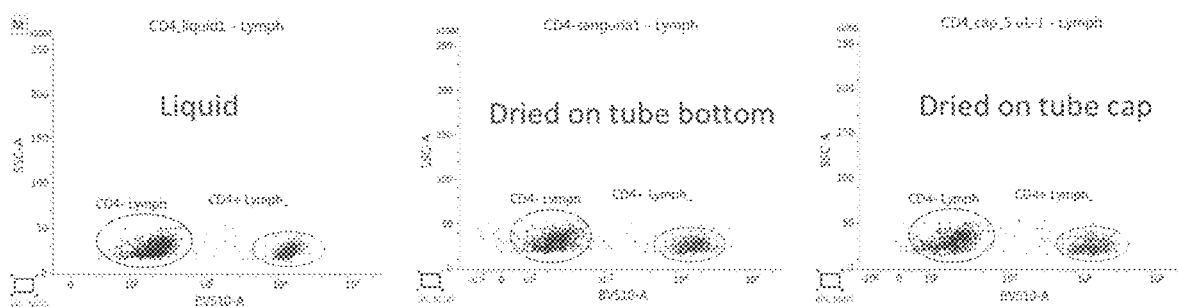
Figure 10C:
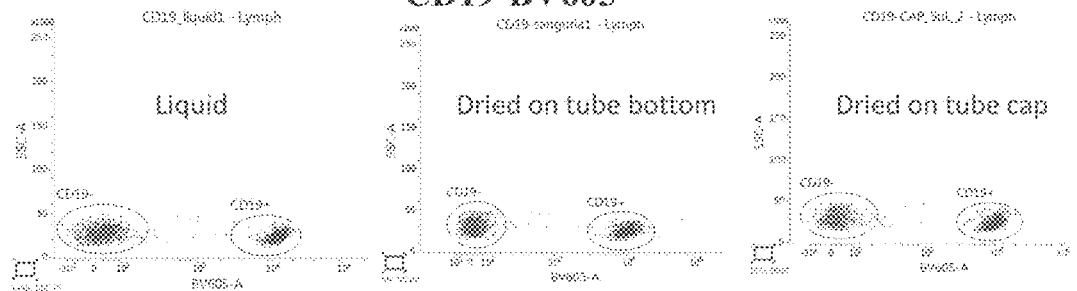

Flow cytometry plots from FACSLyric are provided in FIGS. 8 and 9. Comparing the data obtained from FlowCAP tubes and the positive control, where individual reagents were added just before staining to the BSB buffer, the flow cytometry dotplots are similar for Lymph, T, B, CD4+ T and CD8+ T cells. There is some spreading observed for CD19-BV650 and CD8-BV510 in the data obtained with FlowCAP tube. This is consistent with previous observation for some of the Sirigen dyes after drying. Overall, the FlowCAP tube with deposited dried reagent spots worked as intended in the design.

II. Reagent Recovery from FlowCAP™ Tubes was Measured to Compare Performance of Single Reagent Dried on Tube Cap with Mesh and on Tube Bottom with Liquid Reagent A. Experiment:

1. Reagent solutions were prepared as follows:

| | | | | | | Deposition Solution | | | |
|---|---|---|---|---|---|---|---|---|---|
| Marker | Fluorochrome | Bulk (mg/mL) | ug/test | Deposition volume (uL) | Deposition concentration (mg/mL) | Bulk volume (uL) | 4X buffer (uL) | DI water (uL) | Total volume (uL) |
| CD4 | BV421 | 0.2 | 0.15 | 5 | 0.03 | 15.0 | 25 | 60.0 | 100 |
| CD4 | BV510 | 0.2 | 0.15 | 5 | 0.03 | 15.0 | 25 | 60.0 | 100 |
| CD19 | BV605 | 0.2 | 0.15 | 5 | 0.03 | 15.0 | 25 | 60.0 | 100 |
| CD4 | BV711 | 0.2 | 0.15 | 5 | 0.03 | 15.0 | 25 | 60.0 | 100 |
| CD4 | BV786 | 0.2 | 0.15 | 5 | 0.03 | 15.0 | 25 | 60.0 | 100 | a. Preparation of FlowCAP and Sangria Tubes with Dried Reagent Spots:

Corning™ Falcon™ Test Tube with Cell Strainer Snap Cap (Corning cat. #352235) were used for reagent deposition.

For each reagent:
i. Deposit 5 μL of solution in the cap of each for a total of 10 tubes
ii. Deposit 5 μL of solution on the bottom of each tube for a total of 10 tubes Tubes were then dried. The tubes were then placed in a pouch with desiccant and stored at room temperature at least overnight before testing.

b. Recovery Testing

50 μl of BDS buffer were added to 3 Flow-CAP tubes for each reagent with dried reagent on the cap, soaked for 3 min and then centrifuged at 1000×g for 5 min. 150 μL of PBS was then added to the bottom of the tube.

For the control, to 3 tubes for each reagent with dried reagent spots on the bottom was added 50 μL of BSB buffer (BD Brilliant Stain Buffer, BD Biosciences, San Jose, CA), following which the tubes were centrifuged at 1000×g for 5 min. 150 μL of PBS was added to the bottom of the tube.

120 μL of liquid from each tube was introduced into a black 96 well plate, the fluorescence signal was measured on a fluorescence plate reader (SpectroMax M5) from each well and the recovery was calculated based on fluorescence signal measured with the liquid reagent solution.

B. Results:

Recovery rate measured by fluorescence intensity was found to be in the range of 70-90%. See table below of the reagent recovery of reagent dried on the tube cap and tube bottom using liquid reagent as the control (100%).

| | BV421 | BV510 | BV605 | BV711 | BV786 |
|---|---|---|---|---|---|
| Flow-cap | 74% | 97% | 78% | 91% | 68% |
| | 74% | 92% | 71% | 86% | 73% |
| | 69% | 86% | 73% | 85% | 76% |

-continued

|  | BV421 | BV510 | BV605 | BV711 | BV786 |
|---|---|---|---|---|---|
| Tube-bottom | 114% | 95% | 87% | 101% | 94% |
|  | 96% | 103% | 123% | 99% | 101% |
|  | 90% | 101% | 90% | 100% | 106% |
| Average recovery of reagent dried on tube cap (%) | 72% | 92% | 74% | 87% | 73% |

III. Functional Testing on BD FACSLyric Flow Cytometer

A. Experiment:
For each reagent, whole blood staining was tested using the following protocol:
1. Tube with dried reagent on the cap: Add 50 μL of BD BSB buffer into each tube cap with dried reagent and incubate for 3 min at room temperature, centrifuge the tube at 500×g for 5 min to collect the reagent solution to the bottom of the tube. Add 50 μL of whole blood to the tube and incubate at room temperature for 30 min. Add 900 μL of BD FACS™ Lysing Solution (BD Biosciences, San Jose, CA) solution and incubate at room temperature for 15 min before analysis on flow cytometer.
2. Tube with dried reagent on the bottom of the tube: Add 50 μL of BD BSB buffer into each tube with dried reagent on the bottom and incubate for 3 min at room temperature. Add 50 μL of whole blood to the tube and incubate at room temperature for 30 min. Add 900 μL of BD FACS™ Lysing Solution and incubate at room temperature for 15 min before analysis on flow cytometer.
3. Control using liquid reagent: Add 5 μL of reagent in liquid form (as described in the table above) and 50 μL of BD BSB buffer into each 12×75 mm test tube. Add 50×L of whole blood to the tube and incubate at room temperature for 30 min. Add 900 μL of BD FACS™ Lysing Solution and incubate at room temperature for 15 min before analysis on flow cytometer.
4. On FACSlyric™ flow cytometer (BD Biosciences, San Jose, CA), gate lymphocytes based on forward and side scatter and then compare the positive and negative lymph populations for each reagent.

B. Results:
The results are shown in FIGS. 10A to E, demonstrating functionality of the dried reagent when present on the cap.
Notwithstanding the appended claims, the disclosure is also defined by the following clauses:
1. A strainer, the strainer comprising:
   a body configured to mate with an open end of the liquid container and having an opening; and
   a filter positioned in the opening, the filter comprising a dried reagent composition.
2. The strainer according to Clause 1, wherein the dried reagent composition comprises a dye.
3. The strainer according to Clause 2, wherein the dye is a polymeric dye.
4. The strainer according to any of the preceding clauses, wherein the filter comprises two or more distinctly positioned dried reagent compositions.
5. The strainer according to any of the preceding clauses, wherein the dried reagent composition is positioned on only one side of the filter.
6. The strainer according to any of the preceding clauses, wherein the filter comprises a mesh.
7. The strainer according to Clause 6, wherein the mesh has a pore size ranging from 10 to 200 μm.
8. The strainer according to Clause 7, wherein the mesh has a pore size ranging from 20 to 100 μm.
9. The strainer according to any of the preceding clauses, wherein the strainer is configured as a cap.
10. The strainer according to Clause 9, wherein the cap is configured to snap fit or screw onto an open end of a container.
11. A cell strainer, the cell strainer comprising:
    a body configured to mate with an open end of the liquid container and having an opening; and
    a mesh positioned in the opening, the mesh comprising first and second distinctly positioned dried dye compositions.
12. The cell strainer according to Clause 11, wherein the dyes of the first and second distinctly positioned dried dye compositions differ from each other by at least one of excitation maxima and emission maxima.
13. The cell strainer according to Clauses 11 or 12, wherein the dyes of the first and second distinctly positioned dried dye compositions are polymeric dyes.
14. The cell strainer according to Clause 13, wherein the polymeric dyes are water soluble conjugated polymers.
15. The cell strainer according to any of Clauses 11 to 14, wherein the dyes of the first and second distinctly positioned dried dye compositions are conjugates of a dye moiety and a specific binding member.
16. The cell strainer according to Clause 15, wherein the specific binding member comprises an antibody or binding fragment thereof.
17. The cell strainer according to any of Clauses 11 to 16, wherein the cell strainer comprises three or more distinctly positioned dried dye compositions.
18. The cell strainer according to any of Clauses 11 to 17, wherein the distinctly positioned dried dye compositions are positioned on only one side of the mesh.
19. The cell strainer according to Clause 18, wherein the mesh has a pore size ranging from 10 to 200 μm.
20. The cell strainer according to Clause 19, wherein the mesh has a pore size ranging from 20 to 100 μm.
21. An assembly comprising:
    a liquid container; and
    a strainer according to any of Clauses 1 to 20 mated to the opening of the liquid container.
22. The assembly according to Clause 21, wherein the container is configured to hold a volume ranging from 0.1 ml to 250 ml.
23. The assembly according to Clause 22, wherein the container is a vial.
24. The assembly according to Clause 22, wherein the container is a well of a multi-well plate
25. The assembly according to any of Clauses 21 to 24, wherein the assembly further comprises a dried reagent composition inside of the liquid container.
26. The assembly according to Clause 25, wherein the dried reagent composition is positioned on an inner surface of the liquid container.
27. The assembly according to Clause 25, wherein the dried reagent composition comprises a dried reagent stably associated with a high surface area solid support.
28. The assembly according to Clause 27, wherein the dried reagent composition is retained at a location in the container by a retainer.

29. The assembly according to any of Clauses 21 to 28, further comprising a cover in operable relationship with the filter.
30. The assembly according to Clause 29, wherein the cover is opaque.
31. A method comprising introducing a volume of a liquid into a liquid container through a strainer of an assembly according to any of Clauses 21 to 30 to produce a reconstituted reagent composition.
32. The method according to Clause 31, wherein the liquid comprises a biological sample.
33. The method according to Clause 32, wherein the biological sample comprises whole blood or a fraction thereof.
34. The method according to any of Clauses 31 to 33, wherein the method further comprises assaying the reconstituted reagent composition.
35. The method according to Clause 34, wherein the assaying comprises flow cytometrically analyzing the reconstituted reagent composition.
36. The method according to any of Clauses 31 to 35, wherein the method further comprises storing the reconstituted reagent composition for a period of time.
37. The method according to any of Clauses 31 to 36, wherein the method further comprises shipping the reconstituted reagent composition to a remote location.
38. A kit comprising a strainer according to any of Clauses 1 to 20.
39. The kit according to Clause 38, further comprising a liquid container.
40. The kit according to Clause 39, wherein the container is configured to hold a volume ranging from 0.1 ml to 250 ml.
41. The kit according to Clause 40, wherein the container is a vial.
42. The kit according to Clause 40, wherein the container is a well of a multi-well plate
43. The kit according to any of Clauses 39 to 42, wherein the container further comprises a dried reagent composition inside of the liquid container.
44. The kit according to Clause 43, wherein the dried reagent composition is positioned on an inner surface of the liquid container.
45. The kit according to Clause 44, wherein the dried reagent composition comprises a dried reagent stably associated with a high surface area solid support.
46. The kit according to Clause 45, wherein the dried reagent composition is retained at a location in the container by a retainer.
47. The kit according to any of Clauses 38 to 46, further comprising a cover configured to be associated with the filter.
48. The kit according to Clause 47, wherein the cover is opaque.
49. A method comprising:
    producing a dried reagent composition on a filter of a strainer configured to be mated with an open end of a liquid container.
50. The method according to Clause 49, wherein the dried reagent composition comprises a dye.
51. The method according to Clause 51, wherein the dye is a polymeric dye.
52. The method according to any of Clauses 49 to 51, wherein the method comprises producing two or more distinctly positioned dried reagent composition on the filter.
53. The method according to Clause 52, wherein the two or more distinctly positioned dried reagent compositions comprise first and second distinctly positioned dried dye compositions.
54. The method according to Clause 53, wherein the dyes of the first and second distinctly positioned dried dye compositions differ from each other by at least one of excitation maxima and emission maxima.
55. The method according to Clauses 53 or 54, wherein the dyes of the first and second distinctly positioned dried dye compositions are polymeric dyes.
56. The method according to Clause 55, wherein the polymeric dyes are water soluble conjugated polymers.
57. The method according to any of Clauses 53 to 56, wherein the dyes of the first and second distinctly positioned dried dye compositions are conjugates of a dye moiety and a specific binding member.
58. The method according to Clause 57, wherein the specific binding member comprises an antibody or binding fragment thereof.
59. The method according to any of Clauses 53 to 58, wherein the cap comprises three or more distinctly positioned dried dye compositions.
60. The method according to any of Clauses 49 to 59, wherein the dried reagent composition is positioned on only one side of the filter.
61. The method according to any of Clauses 49 to 60, wherein the filter comprises a mesh.
62. The method according to Clause 61, wherein the mesh has a pore size ranging from 10 to 200 μm.
63. The method according to Clause 62, wherein the mesh has a pore size ranging from 20 to 100 μm.
64. The method according to any of Clauses 49 to 63, wherein the strainer is configured as a cap.
65. The method according to any of Clauses 49 to 63, wherein the cap is configured to snap fit or screw onto an open end of a container.
66. A cap comprising:
    a body configured to mate with an open end of the liquid container and having an opening; and
    a dried reagent composition associated with the opening such that liquid flowing through the opening into the liquid container reconstitutes the dried reagent composition.
67. The cap according to Clause 66, wherein the dried reagent composition comprises a dye.
68. The cap according to Clause 67, wherein the dye is a polymeric dye.
69. The cap according to any of clauses 66 to 68, wherein the cap comprises two or more distinctly positioned dried reagent compositions.
70. The cap according to any of Clauses 66 to 68, wherein the cap includes one or more open bottomed wells comprising a dried reagent composition present therein.
71. The cap according to Clause any of Clauses 66 to 70, wherein the cap is configured to snap fit or screw onto an open end of a container.
72. A method comprising introducing a volume of a liquid into a liquid container through a cap according to any of Clauses 66 to 71 to produce a reconstituted reagent composition.
73. The method according to Clause 72, wherein the liquid comprises a biological sample.
74. The method according to Clause 73, wherein the biological sample comprises whole blood or a fraction thereof.

75. The method according to any of Clauses 72 to 74, wherein the method further comprises assaying the reconstituted reagent composition.
76. The method according to Clause 75, wherein the assaying comprises flow cytometrically analyzing the reconstituted reagent composition.
77. The method according to any of Clauses 72 to 76, wherein the method further comprises storing the reconstituted reagent composition for a period of time.
78. The method according to any of Clauses 72 to 77, wherein the method further comprises shipping the reconstituted reagent composition to a remote location.
79. A kit comprising a cap according to any of Clauses 66 to 71.
80. The kit according to Clause 79, further comprising a liquid container.
81. The kit according to Clause 80, wherein the container is configured to hold a volume ranging from 0.1 ml to 250 ml.
82. The kit according to Clause 81, wherein the container is a vial.
83. A method comprising:
    producing a dried reagent composition on a cap configured to be mated with an open end of a liquid container.
84. The method according to Clause 83, wherein the dried reagent composition comprises a dye.
85. The method according to Clause 84, wherein the dye is a polymeric dye.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A strainer, the strainer comprising:
   a body configured to mate with an open end of a liquid container and having an opening; and
   a filter positioned in the opening, the filter comprising a dried reagent composition comprising a dye.

2. The strainer according to claim 1, wherein the dye is a polymeric dye.

3. The strainer according to claim 1, wherein the filter comprises two or more distinctly positioned dried reagent compositions.

4. The strainer according to claim 1, wherein the dried reagent composition is positioned on only one side of the filter.

5. The strainer according to claim 1, wherein the filter comprises a mesh.

6. The strainer according to claim 1, wherein the strainer is configured as a cap.

7. The strainer according to claim 6, wherein the cap is configured to snap fit or screw onto an open end of the liquid container.

8. An assembly comprising:
   a liquid container; and
   a strainer, the strainer comprising:
   a body mated to an open end of the liquid container and having an opening; and
   a filter positioned in the opening, the filter comprising a dried reagent composition comprising a dye.

9. The assembly according to claim 8, wherein the liquid container is configured to hold a volume ranging from 0.1 ml to 250 ml.

10. The assembly according to claim 8, wherein the assembly further comprises a dried reagent composition inside of the liquid container.

11. The assembly according to claim 10, wherein the dried reagent composition is positioned on an inner surface of the liquid container.

12. The assembly according to claim 10, wherein the dried reagent composition comprises a dried reagent stably associated with a high surface area solid support.

13. The assembly according to claim 8 further comprising a cover in operable relationship with the filter.

14. The assembly according to claim 13, wherein the cover is opaque.

15. A method comprising introducing a volume of a liquid into a liquid container through a strainer of an assembly according to claim 8 to produce a reconstituted reagent composition.

16. The method according to claim 15, wherein the liquid comprises a biological sample.

17. The method according to claim 16, wherein the biological sample comprises whole blood or a fraction thereof.

18. The method according to claim 15, wherein the method further comprises assaying the reconstituted reagent composition.

19. The method according to claim 18, wherein the assaying comprises flow cytometrically analyzing the reconstituted reagent composition.

* * * * *